US012758405B2

(12) United States Patent
Sankai et al.

(10) Patent No.: US 12,758,405 B2
(45) Date of Patent: Oct. 13, 2026

(54) WEARABLE HAND-FINGER MOTION SUPPORT APPARATUS

(71) Applicant: CYBERDYNE Inc., Tsukuba (JP)

(72) Inventors: Yoshiyuki Sankai, Tsukuba (JP); Dan Yoshikawa, Tsukuba (JP)

(73) Assignee: CYBERDYNE Inc., Ibaraki (JP)

( * ) Notice: Subject to any disclaimer, the term of this patent is extended or adjusted under 35 U.S.C. 154(b) by 958 days.

(21) Appl. No.: 18/003,885

(22) PCT Filed: Jun. 30, 2021

(86) PCT No.: PCT/JP2021/024820
§ 371 (c)(1),
(2) Date: Dec. 29, 2022

(87) PCT Pub. No.: WO2022/004810
PCT Pub. Date: Jan. 6, 2022

(65) Prior Publication Data

US 2023/0263644 A1 Aug. 24, 2023

(30) Foreign Application Priority Data

Jun. 30, 2020 (JP) ................................ 2020-113226

(51) Int. Cl.
*A61F 2/72* (2006.01)
*A61F 2/54* (2006.01)
(Continued)

(52) U.S. Cl.
CPC ................ *A61F 2/586* (2013.01); *A61F 2/72* (2013.01); *A61F 5/013* (2013.01); *A61H 1/0288* (2013.01); *A61F 2002/587* (2013.01); *A61F 2002/701* (2013.01); *A61F 2002/704* (2013.01); *A61F 2002/7635* (2013.01); *A61F 2002/764* (2013.01); *A61F 2005/0155* (2013.01); *A61F 2005/0188* (2013.01); *A61H 2230/085* (2013.01)

(58) Field of Classification Search
None
See application file for complete search history.

(56) References Cited

U.S. PATENT DOCUMENTS

2012/0029399 A1 2/2012 Sankai
2020/0345574 A1 11/2020 Sankai

FOREIGN PATENT DOCUMENTS

JP 2010240285 A 10/2010
KR 1020190081891 A 7/2019
(Continued)

OTHER PUBLICATIONS

International Search Report for related PCT Application No. PCT/JP2021/024820, filed Jun. 30, 2021, 5 pages.

*Primary Examiner* — David H Willse
(74) *Attorney, Agent, or Firm* — Procopio, Cory, Hargreaves & Savitch LLP

(57) ABSTRACT

A wearer is made to judge, based on a detection result by a signal detection unit, either one of an opposition movement, an adduction movement, a flexion movement, and an extension movement of a thumb; and a linear member drive unit is controlled to pull or relax each linear member corresponding to the judged movement in order to cause the thumb's intrinsic muscles and/or extrinsic muscles, which are required for the judged movement, to generate an assist force.

8 Claims, 27 Drawing Sheets

(51) Int. Cl.

| | |
|---|---|
| ***A61F 2/58*** | (2006.01) |
| ***A61F 5/01*** | (2006.01) |
| ***A61H 1/02*** | (2006.01) |
| *A61F 2/70* | (2006.01) |
| *A61F 2/76* | (2006.01) |

(56) References Cited

FOREIGN PATENT DOCUMENTS

| | | | | | |
|---|---|---|---|---|---|
| WO | 2018055812 | A1 | | 3/2018 | |
| WO | WO 2020/122792 | A1 | * | 6/2020 | ............... A61F 2/72 |

* cited by examiner (A) (B) (C)

(A)

(B)

(C)

(B)

(A)

(A)

(B)

(B)

(A)

(A)

(B)

(A)

(B)

(A)

(B)

WEARABLE HAND-FINGER MOTION SUPPORT APPARATUS

CROSS-REFERENCE TO RELATED APPLICATIONS

This application is a US national stage application of International Application PCT/JP2021/024820, filed Jun. 30, 2021, which claims benefit of priority from Japanese Patent Application JP 2020-113226, filed Jun. 30, 2020, the contents of which are incorporated by reference.

TECHNICAL FIELD

The present invention relates to a wearable hand-finger motion support apparatus and, particularly, the invention is suited for application to a motion support apparatus that supports a person who has hand-finger paralysis, from among upper-limb functional disabilities, to perform daily motions.

BACKGROUND ART

Particularly the hand-finger paralysis, among the upper-limb functional disabilities, makes it difficult to perform daily-life motions such as holding/gripping a daily item(s), and significantly degrades the QOL (Quality of Life) of the person who has the hand-finger paralysis. Movements of a thumb (or pollex) are very important in order to hold/grip an object.

However, if a cerebrovascular disease or a spinal cord injury causes a motor function of a hand and fingers to degrade and thereby causes the hand-finger paralysis, the person can no longer bend or extend the finger(s) or move the thumb to an opposite position and it becomes difficult to hold/grip any object in everyday life.

Accordingly, there has been proposed and developed hand-finger motion support equipment for supporting the daily life motions such as holding a daily item(s) by supporting the hand-finger motions of the person who has the hand-finger paralysis. For example, the inventors of the present application propose a motion support apparatus capable of giving a sufficient force for practical use to retain a polyarticular structure when performing a flexion motion, and supporting the flexion motion and extension motion which are sufficient for practical use with a simple configuration (see PTL 1).

CITATION LIST

Patent Literature

PTL 1: WO2018/055812

SUMMARY OF THE INVENTION

Problems to be Solved by the Invention

The motion assistance apparatus as in PTL 1 is designed to cause the polyarticular structure to perform the bending motion or the extension motion by pulling or relaxing linear members in accordance with a wearer's intention; and it is useful to support the motion to hold/grip a rigid cylindrical object.

However, there are various shapes and materials of daily items which become targets to be gripped, so that the humans hold or grip the daily items by means of not only simple motions and force information, but also mechanical properties such as skin deformation and fingerprints, tactile information to know the quality of materials, and various hand-finger shapes.

Therefore, it is important for a finger pulp(s) to directly contact an object and also a plurality of pieces of sensory information including the hand-finger shapes are important to support the gripping motion. Particularly, a thumb is independent from other four fingers and serves a very important role to hold/grip the object.

In order to grip the object, it is necessary to bend the fingers, touch the surface of the object, and apply a force to it. Gripping in many cases such as power gripping and pinching is realized by opening the thumb toward the side opposite the other four fingers and fixing the target object with the thumb and the other fingers. Also, lateral gripping which is used when gripping a thin object such as a key is implemented with the thumb and side faces of an index finger by performing adduction of the thumb.

Accordingly, many thumb's movements relating to the gripping are indispensable for the human's gripping movements; and if the hand-finger paralysis such as a motor functional disability or a sensory disturbance occurs due to a cerebrovascular disease or a spinal cord injury, basic motions such as the finger's bending and stretching movements and/or the opposition movement of the thumb can no longer performed and it becomes difficult to grip things in everyday life.

Actually, the decline in the thumb's functions accounts for about 40% of the decline in the hand's functions. Therefore, conventional motion support apparatuses which only assist the thumb's flexion and extension, narrows grip types by fixing the thumb at the opposite position, or increases the weight by using links or frames cannot obtain the effects for the use in the everyday life and there is fear that the QOL (Quality of Life) of a person with the hand-finger paralysis who has the hand-finger motor functions may degrade significantly.

The present invention was devised in consideration of the above-described circumstances and aims at proposing a wearable hand-finger motion support apparatus capable of assisting the thumb's movements without impeding the degree of freedom of the thumb when holding/gripping the target object in everyday life.

Means to Solve the Problems

In order to solve the above-described problems, there is provided according to the present invention a wearable hand-finger motion support apparatus including: a first retaining member mounted to cover a tip of a wearer's thumb; a second retaining member mounted to be wound around a proximal phalanx of the thumb; a third retaining member mounted to retain a root of the thumb and a wrist leading to the root in close contact with each other; a plurality of linear members, one end of which is fixed to either the first retaining member or the second retaining member, and each of which is routed through the third retaining member along a surface of the thumb and is extended; a linear member drive unit that drives an extended portion of each linear member to pull or relax the extended portion of each linear member; a signal detection unit that is located on a body surface corresponding to intrinsic muscles and/or extrinsic muscles of the wearer's thumb and detects an EMG signal or a biosignal to cause the thumb to perform motions; a movement judgment unit that judges either one of an opposition movement, an adduction movement, a flexion movement, or an extension movement of the thumb by the wearer on the basis of a detection result by the signal detection unit; and a drive control unit that controls the linear member drive unit to pull or relax each linear member corresponding to the movement judged by the movement judgment unit in order to cause the intrinsic muscles and/or the extrinsic muscles of the thumb, which are required for the movement judged by the movement judgment unit, to generate an assist force.

As a result, when gripping a target object in everyday life, the wearable hand-finger motion support apparatus can assist motions of not only the flexion movement and the extension movement of the thumb, but also the opposition movement and the adduction movement of the thumb.

Furthermore, according to the present invention, the plurality of linear members are fixed to the second retaining member and have an opposition movement wire and an adduction wire which are respectively pulled out from the proximal phalanx of the thumb and are routed through the third retaining member toward a direction along an opponens pollicis muscle and an adductor pollicis muscle existing in a palm including the thumb; wherein the signal detection unit detects the EMG signal or the biosignal from the body surface corresponding to the opponens pollicis muscle and the adductor pollicis muscle among the intrinsic muscles of the thumb; wherein the movement judgment unit judges the opposition movement or the adduction movement of the thumb by the wearer on the basis of the detection result by the signal detection unit; and wherein the drive control unit controls the linear member drive unit to alternately pull or relax the opposition movement wire or the adduction wire in synchronization with timing to start the opposition movement or the adduction movement of the thumb as judged by the movement judgment unit.

As a result, the wearable hand-finger motion support apparatus can assist motions along a muscle contraction direction to implement the opposition movement or the adduction movement of the wearer's thumb by controlling the linear member drive unit to alternately pull or relax the opposition movement wire or the adduction wire in synchronization with the timing to start the opposition movement or the adduction movement of the thumb.

Furthermore, according to the present invention, the linear member drive unit: is provided on a separate body from the first retaining member to the third retaining member; includes a first pulley with a specified diameter to which respective extended portions of the opposition movement wire and the adduction wire that are pulled out from the second retaining member as a base point are fixed and connected, and a first actuator with its output axis which engages with the first pulley; and causes a rotating force of the output axis of the first actuator to be transmitted to the opposition movement wire or the adduction wire via the first pulley.

As a result, with the wearable hand-finger motion support apparatus, the linear member drive unit is designed to have a wire drive configuration using the actuator, so that the opposition movement wire and the adduction wire can be instantly wound only by rotary drive of the output axis of the actuator and also the linear member drive unit, the drive control unit, etc. can be installed at positions separate from the first to third retaining members via the opposition movement wire and the adduction wire.

Furthermore, according to the present invention, the linear member drive unit has a slide retaining unit which retains the first pulley and the first actuator so that the first pulley and the first actuator can freely slide integrally with each other; wherein the first slide retaining unit is connected to the third retaining member via a fixed-length tube into which the opposition movement wire and the adduction wire are inserted respectively; and wherein lengths of the opposition movement wire and the adduction wire between the first retaining member and the second retaining member can be adjusted by causing the first pulley and the first actuator to slide relative to the slide retaining unit.

As a result, the wearable hand-finger motion support apparatus can freely adjust the distance between the first retaining member and the second retaining member in accordance with the length of the thumb simply by causing the first pulley and the first actuator, which are retained by the slide retaining unit, to slide.

Furthermore, according to the present invention, the plurality of linear members are fixed to the first retaining member and have a flexion wire and the extension wire, which are pulled out from the tip of the thumb and are respectively routed through the third retaining member via the second retaining member in directions along a pulp side and a dorsal side; wherein the signal detection unit detects an EMG signal or a biosignal from a body surface corresponding to a flexor pollicis longus muscle and an extensor pollicis longus muscle existing in an upper arm via tendons from the thumb, from among the extrinsic muscles of the thumb; wherein the movement judgment unit judges the flexion movement or the extension movement of the thumb by the wearer on the basis of the detection result by the signal detection unit; and wherein the drive control unit controls the linear member drive unit to alternately pull or relax the flexion wire or the extension wire in synchronization with timing to start the flexion movement or the extension movement of the thumb as judged by the movement judgment unit.

As a result, the wearable hand-finger motion support apparatus can assist motions along a muscle contraction direction to implement the flexion movement or the extension movement of the wearer's thumb by controlling the linear member drive unit to alternately pull or relax the flexion wire or the extension wire in synchronization with the timing to start the flexion movement or the extension movement of the thumb.

Furthermore, according to the present invention, the linear member drive unit: is provided on a separate body from the first retaining member to the third retaining member; includes a second pulley with a specified diameter to which respective extended portions of the flexion wire and the extension wire that are pulled out from the first retaining member as a base point via the second retaining member are fixed and connected, and a second actuator with its output axis which engages with the second pulley; and causes a rotating force of the output axis of the second actuator to be transmitted to the flexion wire or the extension wire via the second pulley.

As a result, with the wearable hand-finger motion support apparatus, the linear member drive unit is designed to have a wire drive configuration using the actuator, so that the flexion wire and the extension wire can be instantly wound only by rotary drive of the output axis of the actuator and also the linear member drive unit, the drive control unit, etc. can be installed at positions separate from the first to third retaining members via the flexion wire and the extension wire.

Furthermore, according to the present invention, the linear member drive unit has a slide retaining unit which retains the second pulley and the second actuator so that the second pulley and the second actuator can freely slide integrally with each other; wherein the second slide retaining unit is connected to the third retaining member via a fixed-length tube into which the flexion wire and the extension wire are inserted respectively; and wherein lengths of the flexion wire and the extension wire between the first retaining member and the second retaining member can be adjusted by causing the second pulley and the second actuator to slide relative to the slide retaining unit.

As a result, the wearable hand-finger motion support apparatus can freely adjust the distance between the first retaining member and the second retaining member in accordance with the length of the thumb simply by sliding the second pulley and the second actuator which are retained by the slide retaining unit.

Furthermore, according to the present invention, the wearable hand-finger motion support apparatus further includes a polyarticular structure in which links aligned in series are coupled together so as to be rotatable relatively to each other and all the links are integrated together so as to be deformable in a freely bendable manner, wherein the polyarticular structure is provided from the first retaining member, to which one end of the extension wire is fixed, is routed through the second retaining member, and extends to the third retaining member in a state where the extension wire is inserted into each of all the links.

As a result, by providing the polyarticular structure along the first to third retaining members mounted on the wearer's thumb, the wearable hand-finger motion support apparatus can serve a function as a limiter to prevent the thumb from extending too much upon the extension movement of the thumb and also serve a role as a safe protection member to prevent the extension wire from directly contacting the skin surface of the thumb.

Furthermore, according to the present invention, the polyarticular structure is designed so that the links are coupled together so as to be freely separable from each other, and a length of the polyarticular structure can be adjusted by inserting or pulling out a desired number of the links. As a result, the wearable hand-finger motion support apparatus can easily adjust the length in accordance with the joint length of the wearer's thumb.

Furthermore, according to the present invention, the first retaining member has an opening formed therein in order to expose a pulp of the wearer's thumb and the wearable hand-finger motion support apparatus includes: a pressing force estimation unit that estimates a pressing force applied to the pulp of the thumb on the basis of a deformed state of the pulp of the thumb when contacting the object through the opening; and a sensory transmission unit that feeds back and transmits the pressing force, which is estimated by the pressing force estimation unit, as a sensation felt by the pulp of the wearer's thumb.

As a result, the wearable hand-finger motion support apparatus can measure the pressing force applied to the object while making the pulp of the wearer's thumb directly contact the object, which is the target to be gripped, without obstructing the pulp of the wearer's thumb. Accordingly, as the wearer directly contacts and presses the object with the pulp of the thumb, it becomes possible to acquire haptic information regarding the object without disturbing mechanical properties of the skin which prevent deformation or slippage caused in accordance with the shape of the object. Particularly, when the wearer is a person with the hand-finger paralysis, it is very useful because the gripping motion assistance can be implemented based on the haptic information of the thumb.

Furthermore, according to the present invention, the pressing force estimation unit includes: a pair of pressure sensors that are provided at the first retaining member to enter into contact with both side faces of the thumb when being mounted, and respectively detect a pressing force applied from both side faces of the thumb; a relational characteristics derivation unit that measures each of actual measurement values of a plurality levels of load applied to the pulp of the thumb and derives relational characteristics between the load applied to the pulp of the thumb and a detection result of the pair of pressure sensors on the basis of the detection result of the pair of pressure sensors, which is obtained for each actual measurement value; and a calculation estimation unit that calculates and estimates the pressing force applied to the pulp of the thumb when contacting the object on the basis of the relational characteristics calculated by the relational characteristics derivation unit.

Accordingly, the wearable hand-finger motion support apparatus can estimate the gripping force using the thumb by measuring the force on the side faces of the finger as caused by a horizontal-direction deformation of the wearer's thumb.

Furthermore, according to the present invention, the sensory transmission unit includes: a stimulus imparting unit that has terminal groups for imparting physical stimuli to a specified body surface of the wearer; a transmission setting unit that sets a sensory size and a transmission pattern to be transmitted to the wearer according to the pressing force which is applied to the pulp of the thumb and is obtained from the calculation estimation unit; and a stimulus control unit that controls each terminal of each one of the terminal groups for the stimulus imparting unit in accordance with setting content by the transmission setting unit.

As a result, with the wearable hand-finger motion support apparatus, the wearer can recognize the stimulus according to the pressing force applied to the pulp of the thumb as a sensation via a specified body surface.

Furthermore, according to the present invention, the pressing force estimation unit further includes: an acceleration sensor that is provided at the first retaining member so as to be located at a back of the thumb when being mounted and detects acceleration of the thumb in a gripping direction; and a bending resistance estimation unit that estimates bending resistance of the object before entering into contact with the pulp of the thumb on the basis of the detection result by the pair of pressure sensors and a detection result by the acceleration sensor, wherein the transmission setting unit for the sensory transmission unit sets the pressing force estimated by the calculation estimation unit as the sensory size and the transmission pattern to be transmitted to the wearer in a state combined with the bending resistance of the object which is estimated by the bending resistance estimation unit.

Accordingly, the wearable hand-finger motion support apparatus can estimate the bending resistance of the object, which enters into contact with the pulp of the thumb, depending on how much the acceleration of the thumb in the gripping direction reacts from the timing to start the detection by the pair of pressure sensors. Then, the pressing force applied to the pulp of the thumb can be fed back and transmitted to the wearer as a sensation combined with the bending resistance of the object which is the target to be gripped.

Furthermore, the wearable hand-finger motion support apparatus according to the present invention is also applied to one or more fingers of the wearer other than the thumb (a forefinger, a middle finger, a ring finger, and a little finger) in the same manner and wherein the drive control unit controls the linear member drive unit to alternately pull or relax the flexion wire or the extension wire corresponding to a flexion movement or an extension movement of each finger, other than the thumb, on which the first retaining member is mounted in order to cause intrinsic muscles and/or extrinsic muscles of each finger which are required for the flexion movement or the extension movement of the finger to generate an assist force.

As a result, the wearable hand-finger motion support apparatus can construct a system for acquiring the haptic information and performing the gripping motion assistance also for at least one or more fingers other than the thumb of the wearer without impeding the pulp's skin characteristics or the sensory input.

Advantageous Effects of the Invention

According to the present invention, it is possible to implement a wearable hand-finger motion support apparatus capable of assisting the movements of the thumb without impeding the degree of freedom of the thumb when holding/gripping the target object in everyday life.

BRIEF DESCRIPTION OF DRAWINGS

FIGS. 15(A) to 15(C) and 15(*i*) to 15(*iii*) are diagrams for explaining a gripping motion experiment;

DESCRIPTION OF EMBODIMENTS

An embodiment of the present invention will be described below in detail with reference to the drawings.

(1) Motor Functions of Thumb in Human Hand

(1-1) Musculoskeletal System of Hand and Fingers

Figure 1:
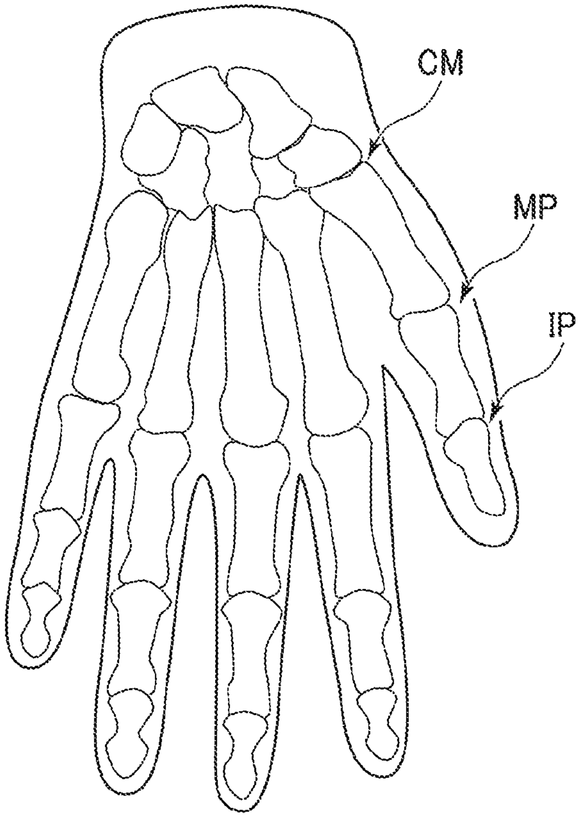
FIG. 1 is a conceptual diagram for explaining the structure of the skeleton and joints of a human hand and fingers.

A thumb's opposition in a human hand is an important function when the human handles articles; and this function enables various types of gripping. FIG. 1 illustrates the skeleton and joints of a thumb on a left hand side. Referring to FIG. 1, the thumb has three joints, that is, a carpometacarpal joint (CM) which is located at the root of a palm and is mainly involved in the thumb's opposition, a metacarpophalangeal joint (MP), and an interphalangeal joint (IP), among which the carpometacarpal joint (CM) is located at the root of the palm and is mainly involved in the thumb's opposition. The carpometacarpal joint (CM) is a saddle-shaped joint with two degrees of freedom and enables the human to acquire a wide range of thumb movements.

Figure 2:
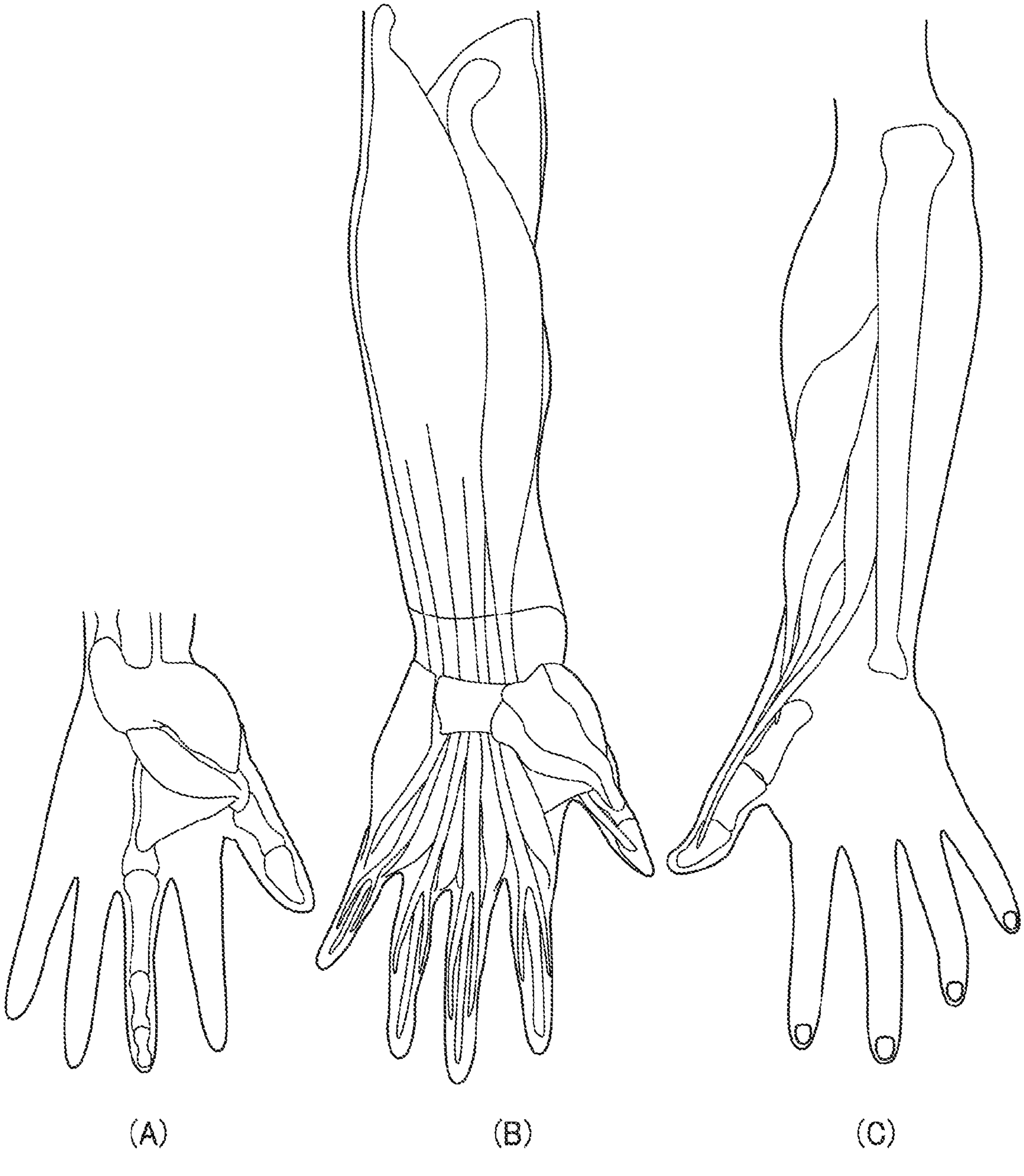
FIGS. 2(A) to 2(C) are conceptual diagrams for explaining the structure of muscles of the human hand and forearm.

FIG. 2(A) to FIG. 2(C) illustrate muscles relating to the thumb's movements. The thumb's movements are controlled by four extrinsic muscles (FPL, APL, EPL, EPB) via tendons and four intrinsic muscles (OP, APB, FPB, ADP) existing in the palm. Incidentally, FIG. 2(A) shows inner muscles based around the root of the thumb, FIG. 2(B)

shows outer muscles on the palm side of the left hand, and FIG. 2(C) shows inner muscles in a forearm of the thumb from a back-of-hand side.

Firstly, an "opposition movement of the thumb" can be realized by coordinated movements of the three muscles, that is, an opponens pollicis muscle (OP), an abductor pollicis brevis muscle (APB), and a flexor pollicis brevis muscle (FPB) which are the intrinsic muscles. Also an "adduction movement of the thumb" involves an adductor pollicis muscle (ADP) which is an adduction muscle. Furthermore, an "abduction movement of the thumb" involves an abductor pollicis brevis muscle (APB) and an abductor pollicis longus muscle (APL).

Furthermore, a "flexion movement of the thumb" involves the flexor pollicis brevis muscle (FPB) and a flexor pollicis longus muscle (FPL). This flexor pollicis brevis muscle (FPB) is a muscle to flex the metacarpophalangeal joint (MP). Also, the flexor pollicis longus muscle (FPL) is a muscle to flex the metacarpophalangeal joint (MP) and the interphalangeal joint (IP) of the thumb.

Furthermore, an "extension movement of the thumb" involves an extensor pollicis brevis muscle (EPB) and an extensor pollicis longus muscle (EPL) which are abduction muscles. This extensor pollicis brevis muscle (EPB) is a muscle to extend the metacarpophalangeal joint (MP) of the thumb and cause the abduction of the thumb; and the extensor pollicis longus muscle (EPL) is a muscle to extend the metacarpophalangeal joint (MP) and the interphalangeal joint (IP) of the thumb and cause the abduction of the thumb.

The present invention was devised because, when the functions of these muscles (the intrinsic muscles and the extrinsic muscles of the thumb) have degraded due to the hand-finger paralysis, the muscles can be substituted by assisting them along contraction directions of these muscles.

(1-2) Essential Functions of Thumb's Movements

The following necessities are required for each of the thumb's movements. Regarding the "opposition movement of the thumb," it is necessary to move the thumb to a position opposite the other four fingers in order to realize gripping which is often used in everyday life, for example, to grip a cylindrical object or a spherical object. Moreover, regarding the "adduction movement of the thumb," it is necessary to assist the adduction of the thumb to move it closer to the index finger in order to realize lateral gripping.

Furthermore, regarding the "flexion movement of the thumb," for the purpose of gripping an object as a basic motion, it is necessary to move the thumb closer to the palm, make the thumb enter into contact with the object, and perform bending and stretching movements to apply a force. Furthermore, regarding the "extension movement of the thumb," it is also necessary to extend the thumb to release the target object.

Now, according to an analysis of daily life motions by using data of the International Classification of Functioning, Disability and Health (ICF), the human's lifting motions account for approximately 40[%] of all the motions. Also, among these motions, a motion to hold an object which weighs 0.5 [kg] accounts for approximately 90[%] of the human's lifting motions. So, the maximum mass of the target object which can be lifted is set as 0.5 [kg].

Figure 3:
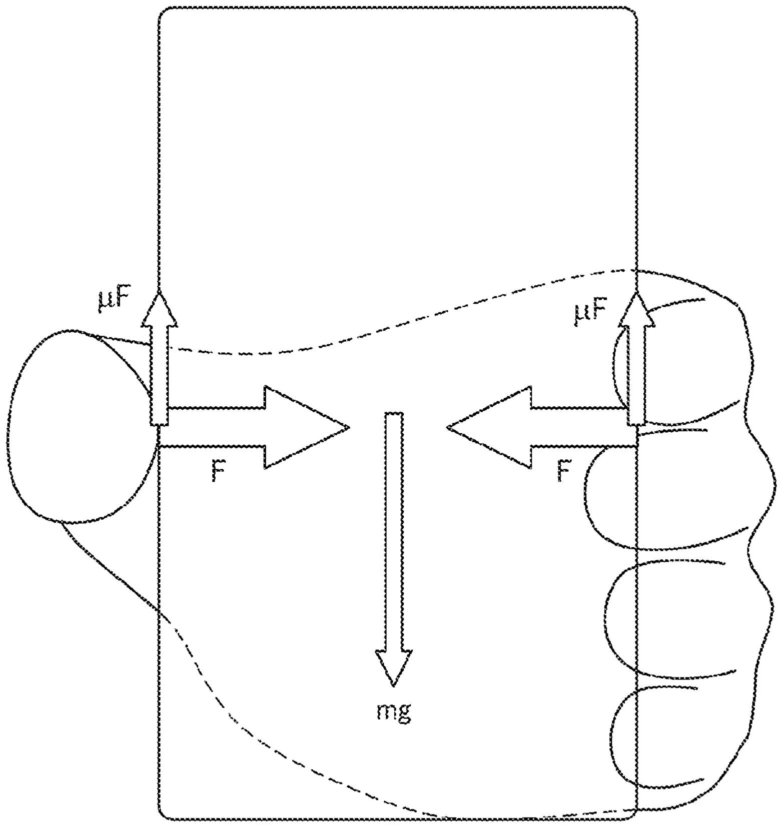
FIG. 3 is a schematic diagram regarding an explanation about lifting power when gripping a target object by using a thumb and a forefinger.

When gripping an object by using the thumb and the forefinger (the index finger) as illustrated in FIG. 3, it has been reported based on experiments in the past that the object is gripped with a force which is approximately 1.4 times as large as the minimum force required to lift the object and the required force can be calculated as indicated in Expression (1) below. In this expression, F represents a gripping force by the thumb and the forefinger, m represents the mass of the object, and μ represents a dynamic friction coefficient.

[Math. 1]

$$F=(mg/2\mu)\times 1.4 \tag{1}$$

Figure 4:
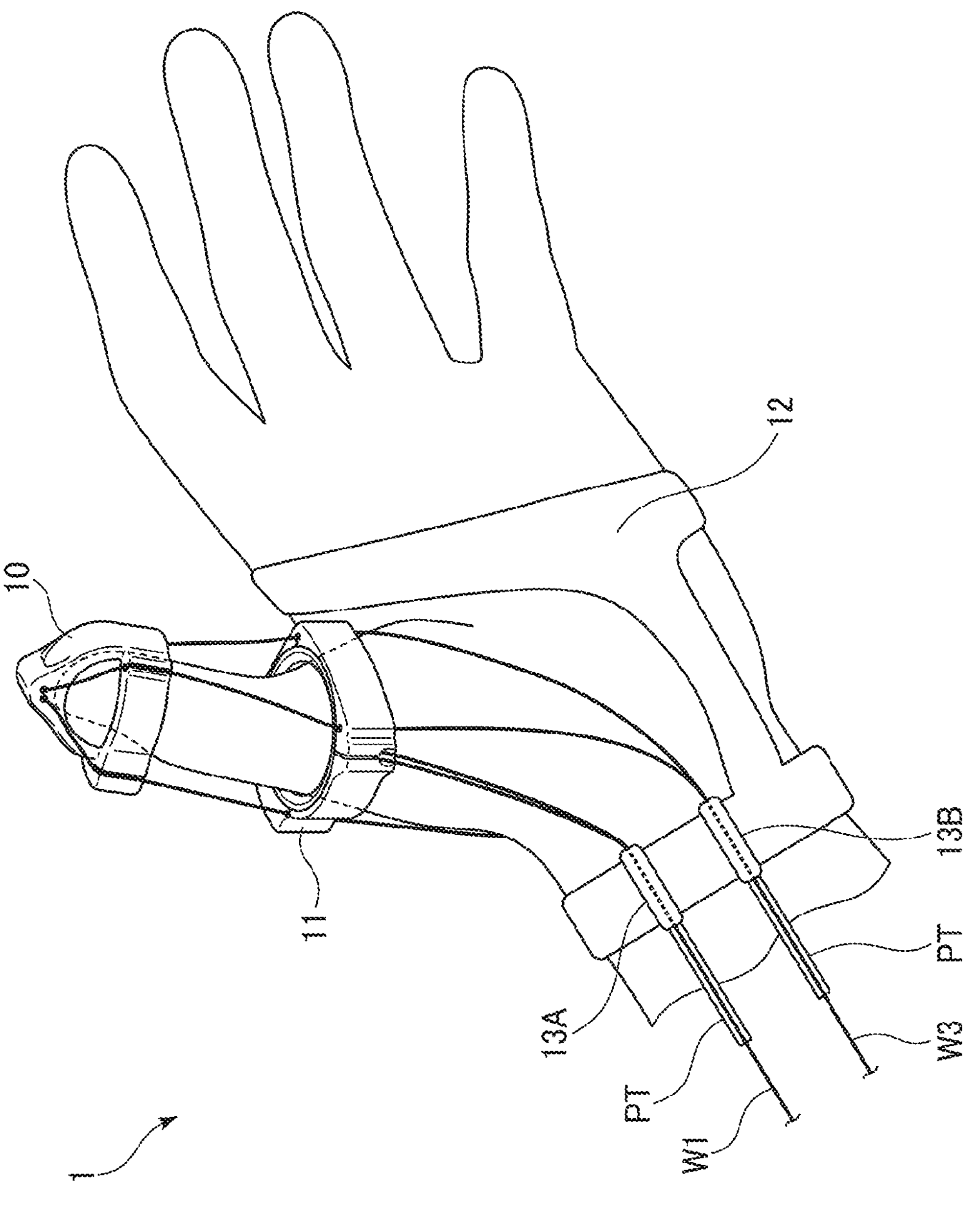
FIG. 4 is a schematic diagram illustrating the configuration of a wearable hand-finger motion support apparatus according to an embodiment of the present invention.
Figure 5:
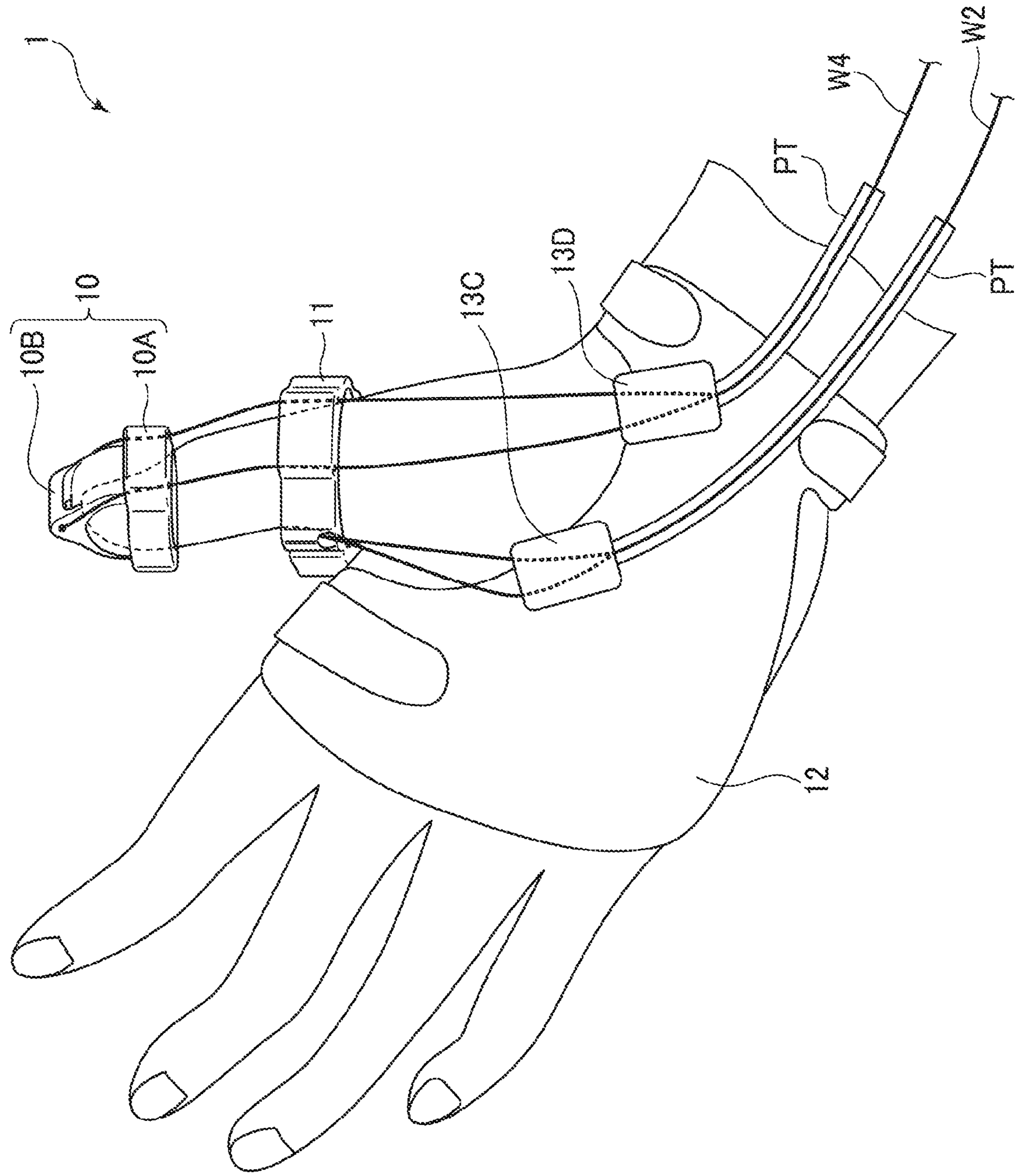
FIG. 5 is a schematic diagram illustrating the configuration of the wearable hand-finger motion support apparatus according to the embodiment of the present invention.

(2) Configuration of Wearable Hand-Finger Motion Support Apparatus According to this Embodiment FIG. 4 and FIG. 5 illustrate a wearable hand-finger motion support apparatus 1 according to this embodiment, which is mounted on the wearer's hand (a left hand in the drawings) and is designed to assist movements according to the two degrees of freedom of the thumb by means of the tendon driving based on an anatomical structure of the hand.

This wearable hand-finger motion support apparatus 1 has: a fingertip retaining unit (a first retaining member) 10 mounted to cover a tip of the wearer's thumb; an auxiliary ring unit (a second retaining member) 11 mounted to be wound around a proximal phalanx of the thumb; and a guiding connection unit (a third retaining member) 13 for a Velcro (registered trademark) glove 12 mounted to retain a root of the thumb and a wrist leading to the root in close contact with each other.

The fingertip retaining unit 10 is made of a polyurethane material as a whole and is structured such that a ring member 10A wound around a distal phalanx of the wearer's thumb and a bridge member 10B which bridges the tip of the thumb with reference to the ring member 10A are integrated together. Both the ring member 10A and the bridge member 10B have notched grooves formed therein at specified positions where wires described later (linear members) can be hooked and fixed.

The auxiliary ring unit 11 is configured so that an outer ring and an inner ring which are both made of a polyurethane material and can be separated from each other are integrated together. The inner ring is wound around the proximal phalanx of the wearer's thumb in close contact with each other and the outer ring has various structures for guiding and hooking the wires or the like.

Incidentally, by setting the dynamic friction coefficient μ in the aforementioned Expression (1) as 0.8 which is the minimum value for the polyurethane material, the required force F which is exerted by the thumb via the fingertip retaining unit 10 and the auxiliary ring unit 11 becomes 4.29 [N].

Figure 6:
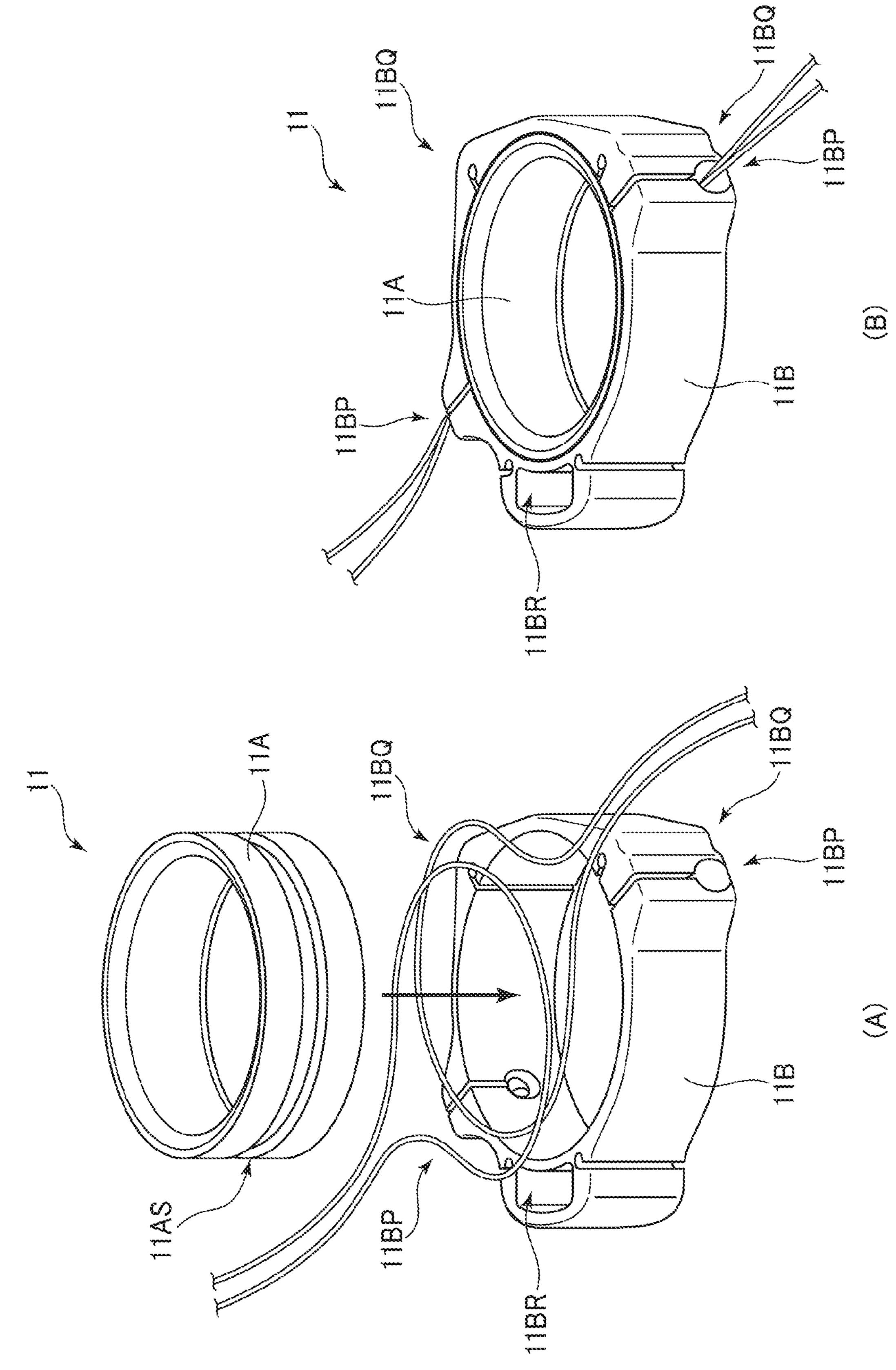
FIGS. 6(A) and 6(B) are perspective views for explaining the configuration of an auxiliary ring unit.

As illustrated in FIG. 6(A) and FIG. 6(B), the auxiliary ring unit 11 is structured such that a ring-shaped inner ring 11A which has an inner diameter according to the proximal phalanx of the thumb, an outer ring 11B which has almost the same inner diameter as an outer diameter of the inner ring 11A are attached so that they can freely engage with each other. Regarding the size diameters of the inner ring 11A and the outer ring 11B, those which can be adapted to the size of the wearer's thumb may be prepared.

The inner ring 11A has an annular notched groove 11AS formed therein along its central outer circumference. The outer ring 11B has a hook groove 11BP formed at a specified position and also a guide groove 11BQ formed at a specified position for the purpose of guiding. It becomes possible to fix and retain a wire via the hook groove 11BP of the outer ring 11B as described later by inserting the inner ring 11A into the outer ring 11B to make them engage with each other in a state where the wire is wound around the notched groove 11AS of the inner ring 11A so that an end point of the wire becomes a circular shape.

Accordingly, the outer ring 11B of the auxiliary ring unit 11 has two annular notched grooves 11BP, two guide grooves 11BQ for guiding wires, and one guide groove 11BR for guiding the polyarticular structure.

Now, an explanation will be provided about a tendon drive system using wires according to the present invention. The wearable hand-finger motion support apparatus 1 is designed to incorporate the idea of imitating contraction of the muscles and traction of tendons and replacing the muscles and the tendons with externally attached wires (linear members).

The wire(s) (linear member(s)) is made of high-strength polyethylene fibers (trade name: Dyneema) with a diameter of 0.5 [mm]; and since the wire itself is very narrow and light-weighted, it does not obstruct the gripping operation.

One end of a plurality of wires is fixed to either the fingertip retaining unit or the auxiliary ring unit and each of the wires is extended by being routed through the guiding connection unit for the Velcro (registered trademark) glove along the surface of the thumb.

In FIG. 4 and FIG. 5 described above, the Velcro (registered trademark) glove 12 is made of a glove of a Magic Tape (registered trademark) material, regarding which the palm and the back of the hand are separated from each other, and is designed to be capable of adjusting a stop position according to the difference of a hand size. The following are attached, as the guiding connection unit (the third retaining member) 13, to the Velcro (registered trademark) glove 12: two wrist-side retaining members 13A, 13B which are fixed to a Magic Tape (registered trademark) band for fixation at the wrist on a surface corresponding to the inside center of the wrist; and two back-of-hand-side retaining members 13C, 13D which are fixed to a surface corresponding to a specified position of the back of the hand in a manner such as they can be attached or detached via the Magic Tape (registered trademark).

Accordingly, the Velcro (registered trademark) glove 12 is structured such that the two wrist-side retaining members 13A, 13B and the two back-of-hand-side retaining members 13C. 13D are fixed and retained as the guiding connection unit 13, so that fine adjustments can be made to adjust a wire pulling direction to an appropriate muscle direction according to the size of the wearer's hand. As a result, the wire pulling direction can be adjusted to the appropriate muscle direction according to the size of the hand.

Regarding the guiding connection unit 13, two wires along the opponens pollicis muscle are pulled out as one opposition movement wire W1 via the wrist-side retaining member 13A from the auxiliary ring unit 11 located at the proximal phalanx of the thumb (FIG. 4) and also two wires along the adductor pollicis muscle are pulled out as one adduction wire W2 via the back-of-hand-side retaining members 13C from the auxiliary ring unit 11 (FIG. 5).

Moreover, regarding the guiding connection unit 13, two wires along the pulp side of the thumb are pulled out as one flexion wire W3 via the wrist-side retaining member 13B from the fingertip retaining unit 10 located at the tip of the thumb (FIG. 4) and also two wires along the dorsal side of the thumb are pulled out as one extension wire W4 via the back-of-hand-side retaining members 13D from the fingertip retaining unit 10 (FIG. 5).

Each of the opposition movement wire W1, the adduction wire W2, the flexion wire W3, and the extension wire W4 is inserted into a protective tube PT, which is made of polytetrafluoroethylene with relatively low friction as an external cylinder, and is designed to prevent, for example, injuries due to frictions on the wearer's hand and wrist as caused by movements of each wire in its lengthwise direction when driving the wire. Each protective tube PT is designed to cover the opposition movement wire W1, the adduction wire W2, the flexion wire W3, and the extension wire W4 from the guiding connection unit 13 to the linear member drive unit 20 (FIG. 7).

Figure 7:
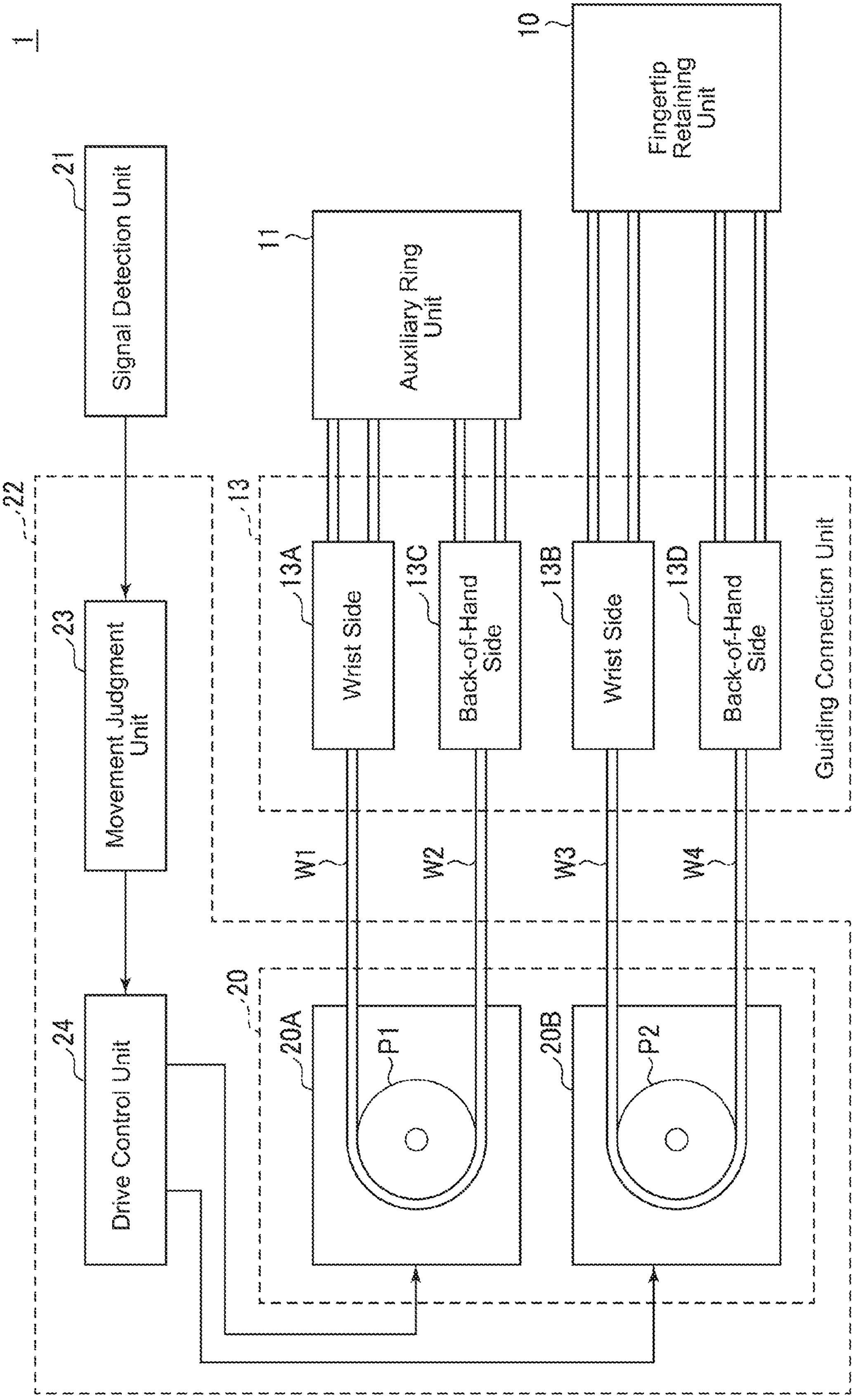
FIG. 7 is a conceptual diagram for explaining a control system for the wearable hand-finger motion support apparatus.

(3) Configuration of Control System for Wearable Hand-Finger Motion Support Apparatus FIG. 7 illustrates the configuration of a control system for the wearable hand-finger motion support apparatus 1 according to this embodiment. The wearable hand-finger motion support apparatus 1 has: the fingertip retaining unit 10, the auxiliary ring unit 11, and the guiding connection unit 13 which are mounted on the wearer's hand and fingers; a signal detection unit 21 located on the wearer's body surface; and an external drive unit 22 which is not mounted on the wearer, but is installed via wire groups W1 to W4.

The signal detection unit 21 detects a neural transmission signal, which is transmitted from the wearer's brain to the thumb, as a biosignal through electrodes located on the body surface corresponding to the intrinsic muscles and/or the extrinsic muscles of the wearer's thumb. Also, the signal detection unit may be designed to detect a myoelectric signal according to the motions of the wearer's thumb together with or instead of the biosignal.

Specifically speaking, the signal detection unit 21 detects a biosignal from the body surface corresponding to the opponens pollicis muscle and the adductor pollicis muscle among the intrinsic muscles of the thumb and also detects an EMG signal or a biosignal from the body surface corresponding to the flexor pollicis longus muscle and the extensor pollicis longus muscle located at the upper arm from the thumb via the tendons among the extrinsic muscles of the thumb.

The external drive unit 22 has a linear member drive unit 20, a movement judgment unit 23, and a drive control unit 24. The linear member drive unit 20 drives extended portions of the respective wire groups (the opposition movement wire, the adduction wire, the flexion wire, and the extension wire) W1 to W4 to pull or relax them.

The linear member drive unit 20 has: a first pulley P1 with a specified diameter to which each of the extended portions of the opposition movement wire W1 and the adduction wire W2 that are pulled out from the auxiliary ring unit 11 as a base point is fixed and connected; and a first actuator 20A whose output axis engages with the first pulley P1. A rotating force of the output axis of the first actuator 20A is transmitted via the first pulley P1 to the opposition movement wire W1 or the adduction wire W2.

Furthermore, the linear member drive unit 20 has: a second pulley P2 with a specified diameter to which each of the extended portions of the flexion wire W3 and the extension wire W4 that are pulled out from the fingertip retaining unit 10 as a base point is fixed and connected; and a second actuator 20B whose output axis engages with the second pulley P2. A rotating force of the output axis of the second actuator 20B is transmitted via the second pulley P1 to the flexion wire W3 or the extension wire W4.

Incidentally, both the first and second actuators 20A, 208 are composed of servo motors capable of torque control and are designed to be capable of instantly switching an assisting direction by changing a rotation direction of the relevant motor.

Each of the movement judgment unit 23 and the drive control unit 24 is composed of a CPU (Central Processing Unit) configuration. The movement judgment unit 23 judges either one of the opposition movement, the adduction movement, the flexion movement, or the extension movement of the thumb by the wearer on the basis of the detection result by the signal detection unit 21.

The movement judgment unit 23 judges the opposition movement or the adduction movement of the thumb by the wearer and also judges the flexion movement or the extension movement of the thumb by the wearer on the basis of the detection result by the signal detection unit 21.

The drive control unit 24 controls the linear member drive unit 20 to cause the intrinsic muscles and/or the extrinsic muscles of the thumb, which are required for the movement judged by the movement judgment unit 23, to generate an assist force and thereby pull or relax each wire (the opposition movement wire, the adduction wire, the flexion wire, and the extension wire) W1 to W4 corresponding to the relevant movement.

Specifically, the drive control unit 24 controls the linear member drive unit 20 to alternately pull or relax the opposition movement wire W1 or the adduction wire W2 in synchronization with the timing to start the opposition movement or the adduction movement of the thumb as judged by the movement judgment unit 23.

On the other hand, the drive control unit 24 controls the linear member drive unit 20 to alternately pull or relax the flexion wire W3 or the extension wire W4 in synchronization with the timing to start the flexion movement or the extension movement of the thumb as judged by the movement judgment unit 23.

Accordingly, the wearable hand-finger motion support apparatus 1 can assist the motions along the muscle contraction direction to make the opposition movement or the adduction movement of the wearer's thumb work by controlling the linear member drive unit 20 in synchronization with the timing to start the opposition movement or the adduction movement of the thumb to alternately pull or relax the opposition movement wire W1 or the adduction wire W2.

Moreover, the wearable hand-finger motion support apparatus 1 can assist the motions along the muscle contraction direction to make the flexion movement or the extension movement of the wearer's thumb work by controlling the linear member drive unit 20 in synchronization with the timing to start the flexion movement or the extension movement of the thumb to alternately pull or relax the flexion wire W3 or the extension wire W4.

(4) Wire Length Adjustment Mechanism of Linear Member Drive Unit

Figure 8:
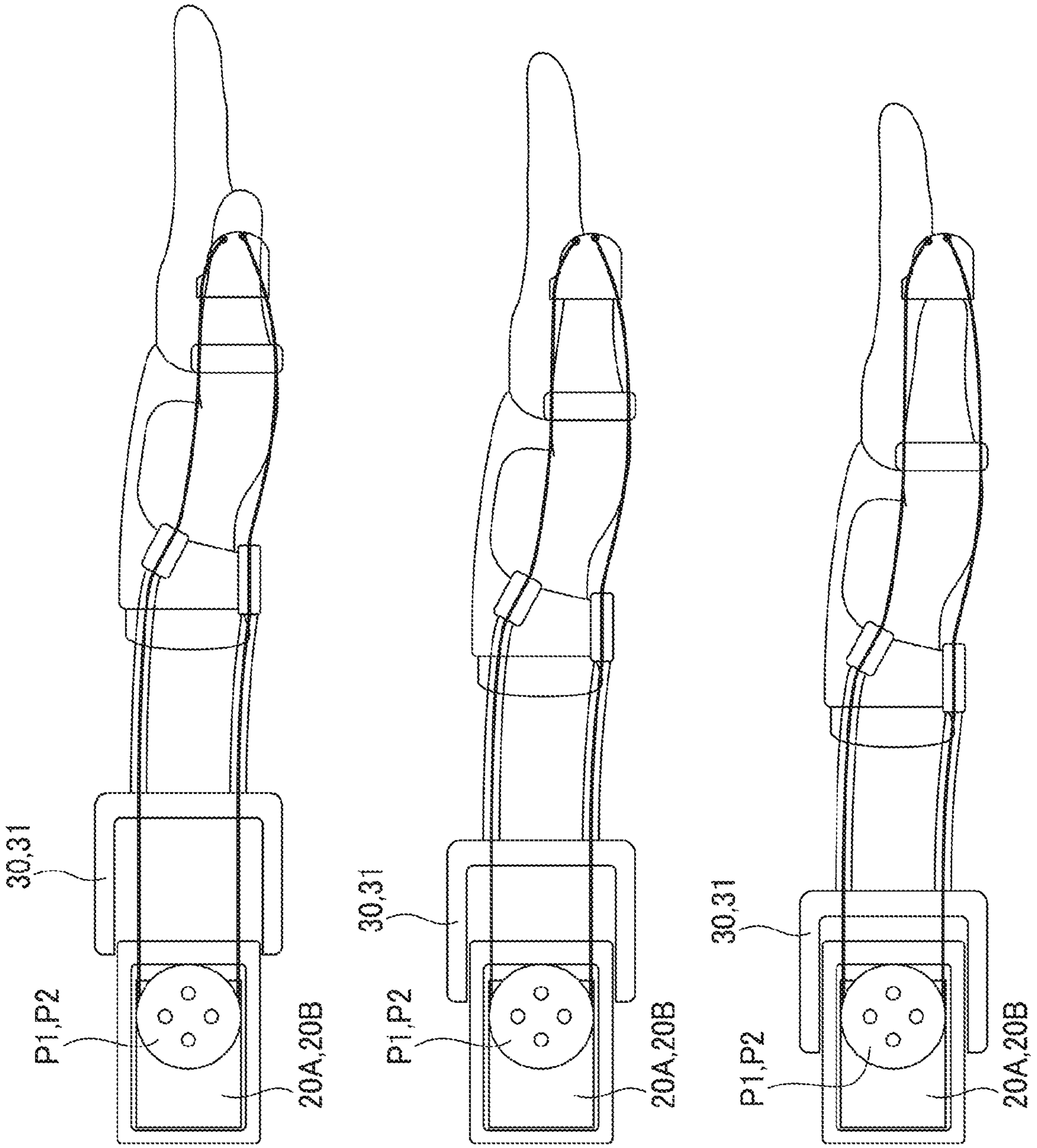
FIGS. 8(A) to 8(C) are conceptual diagrams for explaining a wire length adjustment mechanism of a linear member drive unit.

Referring to FIG. 8(A) to FIG. 8(C), the linear member drive unit 20 has: a first slide retaining unit 30 which retains the first pulley P1 and the first actuator 20A in a manner such that they can freely slide together integrally with each other; and a second slide retaining unit 31 which retains the second pulley P2 and the second actuator 20B in a manner such that they can freely slide together integrally with each other.

The first slide retaining unit 30 is connected to the guiding connection unit 13 via a protective tube PT with a fixed length into which each of the opposition movement wire W1 and the adduction wire W2 is inserted; and the lengths of the opposition movement wire W1 and the adduction wire W2 between the fingertip retaining unit 10 and the auxiliary ring unit 11 can be adjusted by sliding the first pulley P1 and the first actuator 20A relative to the first slide retaining unit 30.

The second slide retaining unit 31 is connected to the guiding connection unit 13 via a protective tube PT with a fixed length into which each of the flexion wire W3 and the extension wire W4 is inserted; and the lengths of the flexion wire W3 and the extension wire W4 between the fingertip retaining unit 10 and the auxiliary ring unit 11 can be adjusted by sliding the second pulley P2 and the second actuator 208 relative to the second slide retaining unit 31.

As a result, with the wearable hand-finger motion support apparatus 1, it becomes possible to freely adjust the distance between the fingertip retaining unit 10 and the auxiliary ring unit 11 according to the length of the wearer's thumb simply by causing the first pulley P1 and the first actuator 20A, which are retained by the first slide retaining unit 20, to slide. Similarly, it becomes possible to freely adjust the distance between the fingertip retaining unit 10 and the auxiliary ring unit 11 according to the length of the wearer's thumb simply by causing the second pulley P2 and the second actuator 20B, which are retained by the second slide retaining unit 31, to slide.

(5) Limiter Function by Polyarticular Structure Designed for Extension Wire

Figure 9:
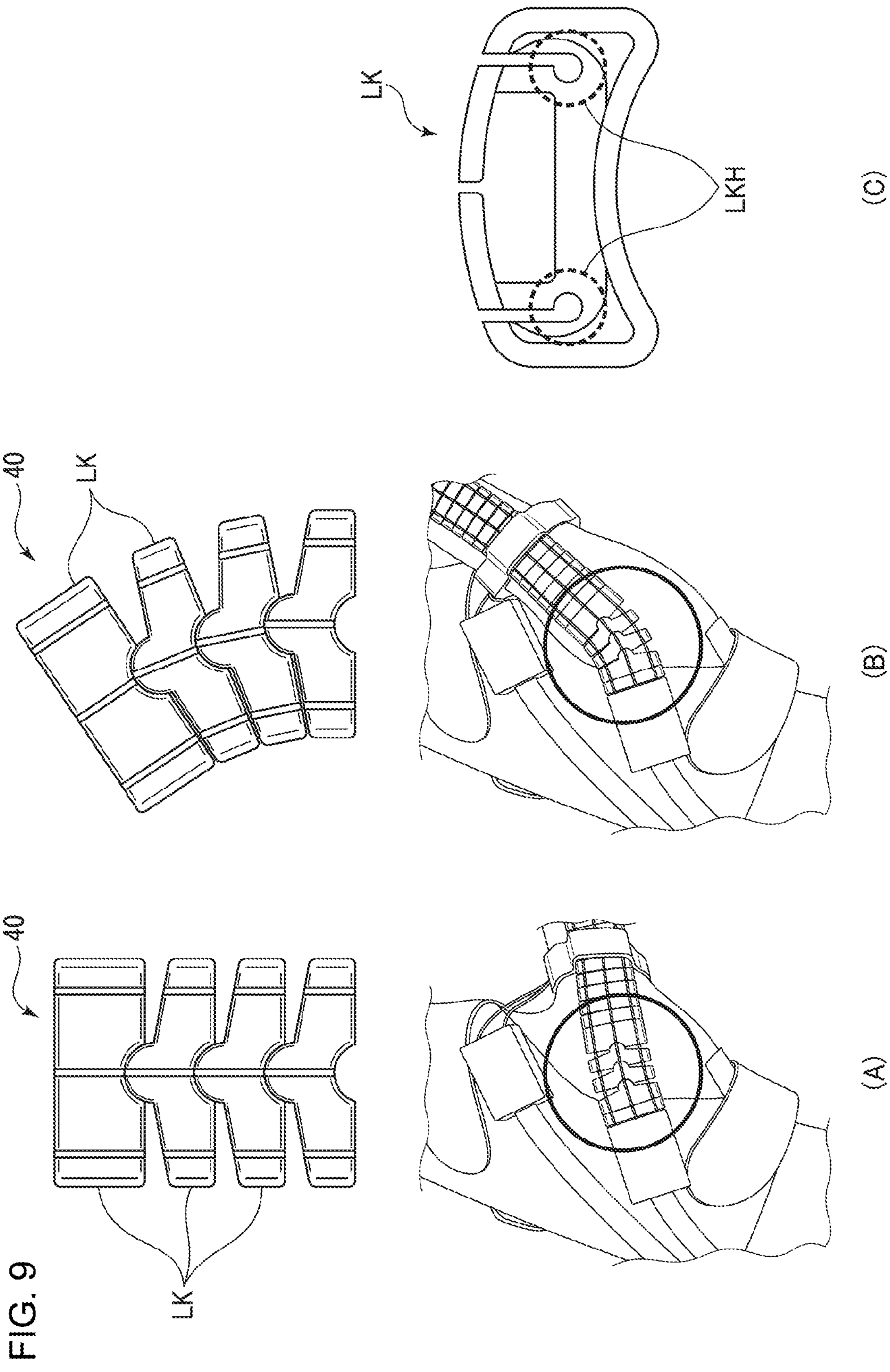
FIGS. 9(A) to 9(C) are explanatory diagrams of a limiter function by a polyarticular structure designed for an extension wire.

Now, the extension wire W4 is designed to protect the wearer's thumb against, for example, injuries which may be caused by sliding of the wires, by covering the extension wire W4 by using a polyarticular structure 40 (FIG. 9) from the fingertip retaining unit 10 through the auxiliary ring unit 11 and then to the guiding connection unit 13.

Specifically, as illustrated in FIG. 9(A) and FIG. 9(B), the polyarticular structure 40 is configured so that links LK aligned in series LK are coupled together so as to be relatively rotatable and all the links LK can freely bend integrally and thereby deform. Referring to FIG. 9(C), each link LK is composed of a cushion member such as polyurethane, which has a hole LKH formed therein for inserting the extension wire W4, and a notch for attaching or detaching the wire is formed in the hole LKH.

This polyarticular structure 40 is provided from the fingertip retaining unit 10, to which one end of the extension wire W4 is fixed, through the auxiliary ring unit 11 and then to the guiding connection unit 13 in a state where the extension wire W4 is inserted into each of all the links LK.

As a result, with the wearable hand-finger motion support apparatus 1, the polyarticular structure 40 is provided along the fingertip retaining unit 10, the auxiliary ring unit 11, and the guiding connection unit 13 which are mounted on the wearer's thumb, so that the polyarticular structure 40 can serve a function as a limiter to prevent the thumb from extending too much upon the extension movement of the thumb and can also serve a role as a safety protection member for preventing the extension wire W4 from directly contacting the skin surface of the thumb.

When the wearer actually abducts the thumb, the axis of the thumb rotates about the carpometacarpal joint (CM). In order to make the polyarticular structure 40 adapt to this angle change of the axis of the thumb, a joint with one degree of freedom is configured by combining a circular protrusion of each link LK with its recess, so that it becomes possible to change the axis orientation of the polyarticular structure by following lateral changes upon the adduction or the abduction while keeping the physical limiter function when the thumb extends.

Furthermore, the polyarticular structure 40 is designed so that the respective links LK are coupled together in a freely separable manner and the length from a link at the top to a link at the end can be adjusted by inserting or removing a desired number of the links LK. As a result, the wearable hand-finger motion support apparatus 1 can easily adjust the length according to the joint length of the wearer's thumb.

(6) Basic Experiments by Thumb Movements and Experiment Results

(6-1) Opposition Movement and Adduction Movement of Thumb

The wearable hand-finger motion support apparatus 1 according to this embodiment is mounted on the wearer's left hand (a hand of the weaker side than their dominant hand) and whether it is possible to assist the opposition movement of the thumb or not is checked by experiments.

Figure 10:
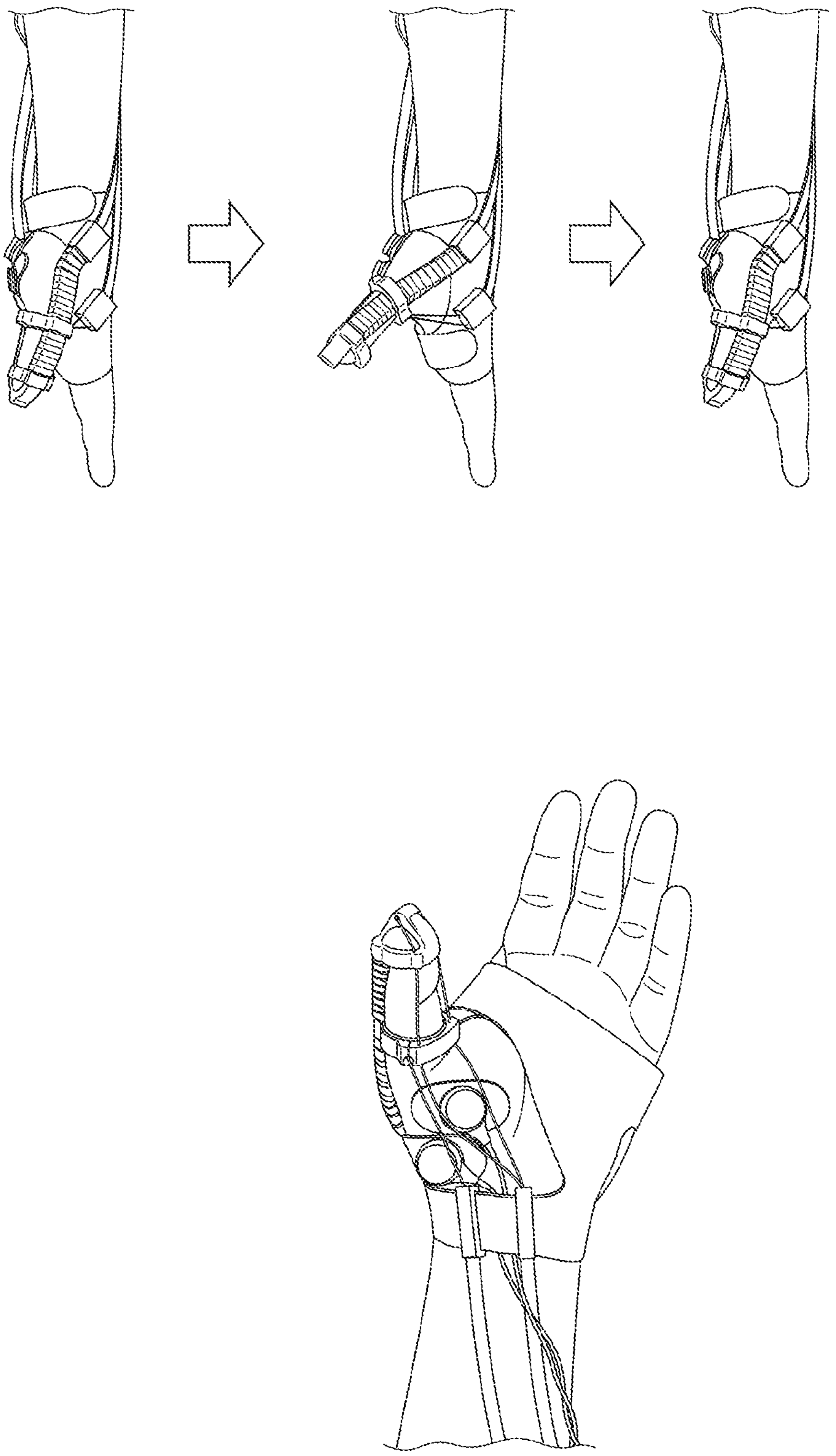
FIGS. 10(A) and 10(B) are diagrams illustrating an experiment of an opposition movement and an adduction movement of the thumb.

Referring to FIG. 10(A), the wearer firstly places the back of their left hand on a desk to keep it in contact with the desk and pulls the opposition movement wire W1 according the opposition movement of the thumb, so that the wearable hand-finger motion support apparatus 1 assists the opposition movement of the thumb.

After the thumb enters into an opposition state 10 seconds after the start of assistance by the wearable hand-finger motion support apparatus 1, the opposition movement wire W1 is relaxed (and the adduction wire W2 is pulled as necessary), thereby making the thumb return to the original arrangement again. When the thumb faces the other four fingers, it is judged that the opposition movement can be performed.

At the same time, electrodes are attached at positions corresponding to the opponens pollicis muscle (OP) and the adductor pollicis muscle (ADP) among the intrinsic muscles of the thumb and the signal detection unit 21 measures a BES (Bio Electric Signal) under resting conditions. Then, whether or not the opposition movement of the thumb is possible only with the support by the wearable hand-finger motion support apparatus 1 is checked (sampling frequency: 1,000 [Hz]; and the number of times of amplification: 200 times). This test was conducted five times by targeting at healthy men without any problems such as disability of the upper limb.

It was confirmed as the result of the above-described experiment that the thumb can be moved to a position opposite the other four fingers as illustrated in FIG. 10(B). Also, it was possible to guide the thumb at the opposite position by using the adduction wire W2 installed on the dorsal side and assist it to return its original arrangement again in all trials.

Figure 11:
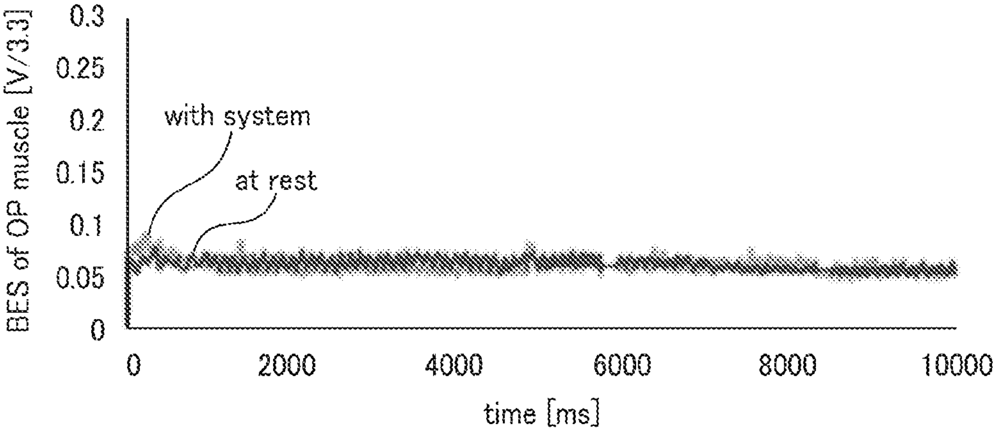
FIGS. 11(A) and 11(B) show graphs indicating experiment results of FIG. 10.
Figure 11:
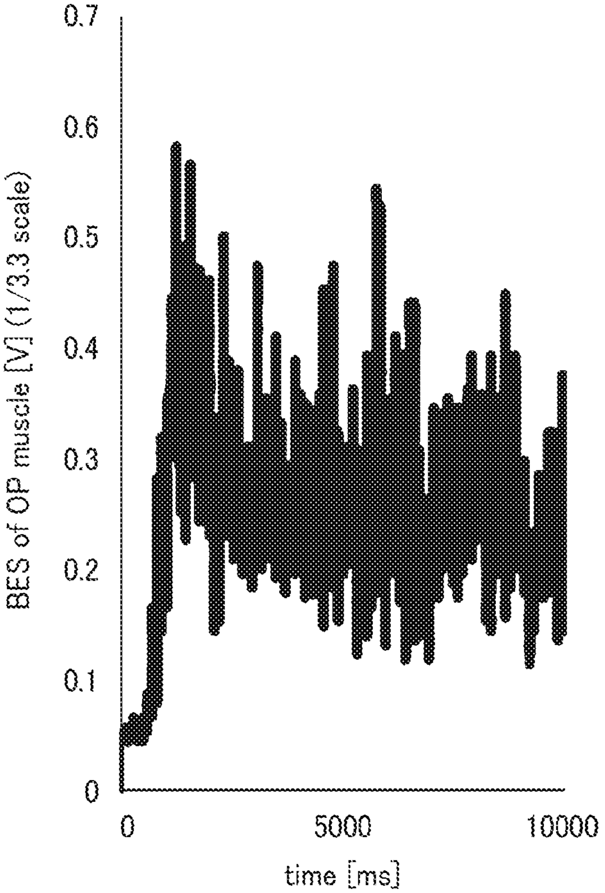

FIG. 11(A) shows a representative example of the BES at that time. When the relevant motion is supported by the present apparatus under resting conditions, an average BES for five seconds, that is, five seconds to 10 seconds after the start of the motion support is calculated. An average BES of the five trials is 0.0691±0.0108 [V] under resting conditions (1/3.3 scale). Then, an average value of the average BES of the five trials in the case with the motion support by the present apparatus (1/3.3 scale) is 0.0615±0.00412 [V]. FIG. 11(B) shows a representative example of the BES when the thumb is moved to the opposite side without using the wearable hand-finger motion support apparatus 1.

(6-2) Flexion Movement and Extension Movement of Thumb

The wearable hand-finger motion support apparatus 1 according to this embodiment is mounted on the wearer's left hand (a hand of the weaker side than their dominant hand) and whether it is possible to assist the flexion movement and the extension movement of the thumb or not is checked by experiments.

Figure 12:
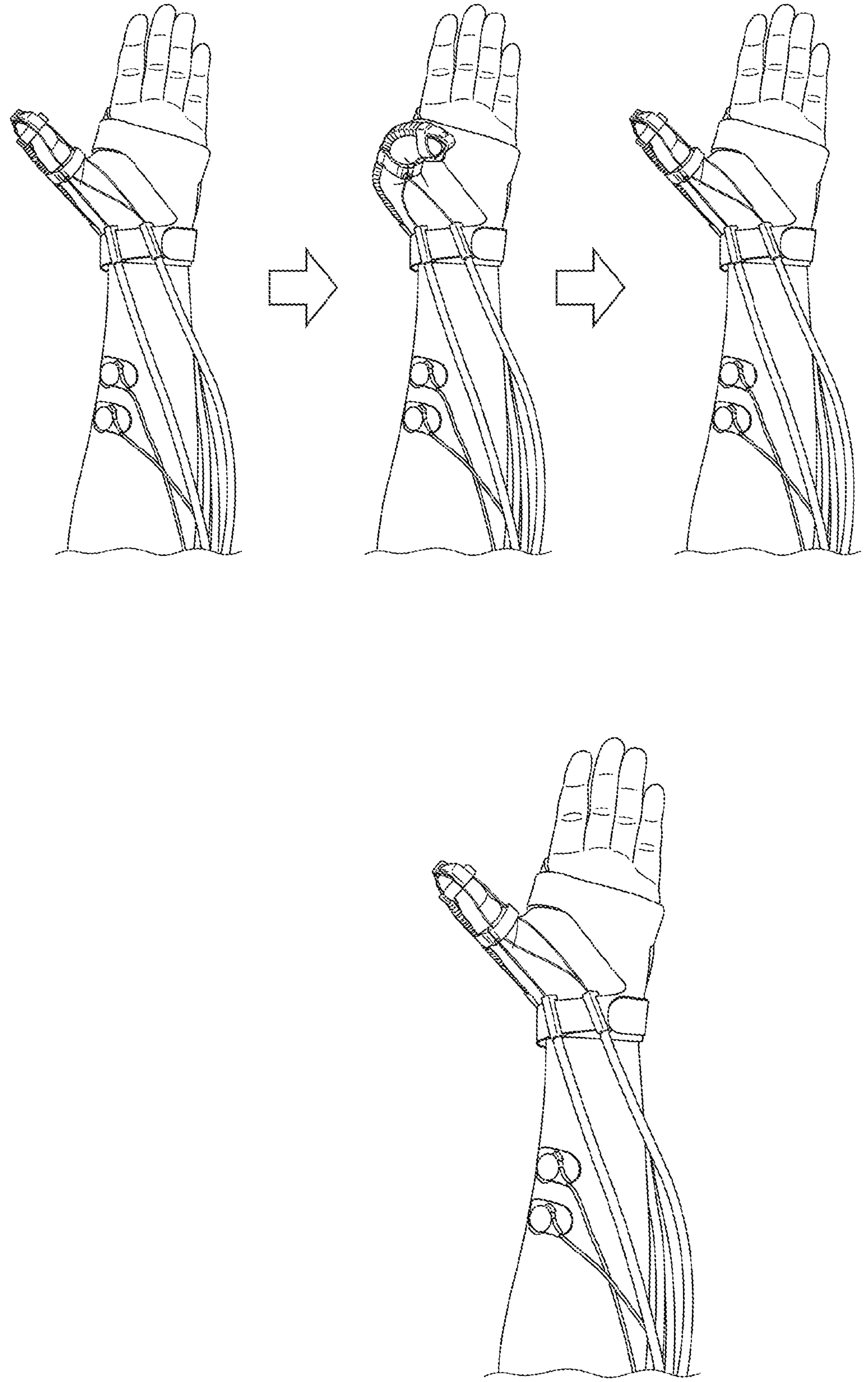
FIGS. 12(A) and 12(B) are diagrams illustrating an experiment of a flexion movement and an extension movement of the thumb.

Referring to FIG. 12(A), the wearer firstly places the back of their left hand on a desk to keep it in contact with the desk and pulls the flexion wire or the extension wire according to the flexion movement or the extension movement of the thumb, so that the wearable hand-finger motion support apparatus 1 assists the flexion movement or the extension movement of the thumb.

The thumb takes a flexion posture 10 seconds after starting the support by the wearable hand-finger motion support apparatus 1; and then the thumb is made to return to an extension posture. At the same time, as illustrated in FIG. 12(A), electrodes are attached to the body surface corresponding to the flexor pollicis longus muscle (FPL) and the extensor pollicis longus muscle (EPL) located at the upper arm via tendons from the thumb and the signal detection unit 21 measures the BES under resting conditions. Then, whether or not the flexion movement or the extension movement of the thumb is possible only with the support by the wearable hand-finger motion support apparatus 1 (the sampling frequency: 1,000 [Hz]; and the number of times of amplification: 200 times). This test was conducted five times by targeting at healthy men without any problems such as disability of the upper limb.

Incidentally, regarding the flexion movement of the thumb, the flexor pollicis brevis muscle (FPB) for flexing the carpometacarpal joint (CM) exists in the palm; however, since the electrodes obstruct the flexion movement itself this time, the electrodes are located at the position of the flexor pollicis longus muscle (FPL).

Figure 13:
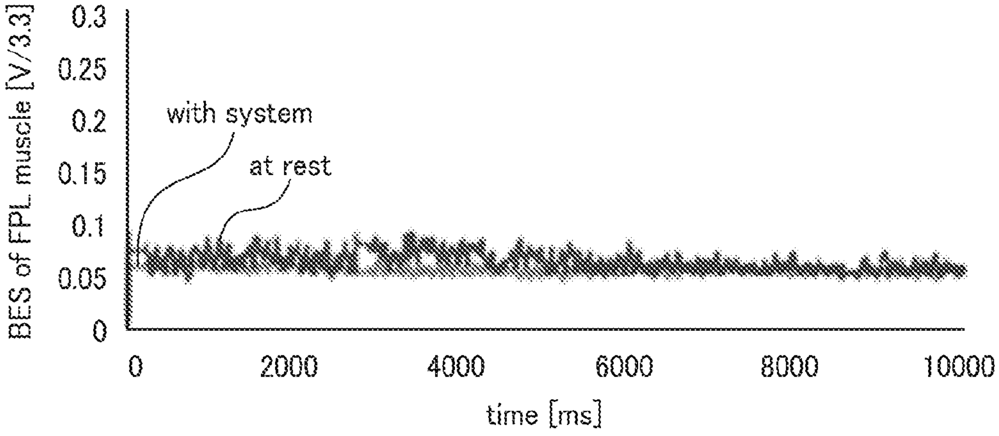
FIGS. 13(A) and 13(B) show graphs indicating experiment results of FIG. 12.
Figure 13:
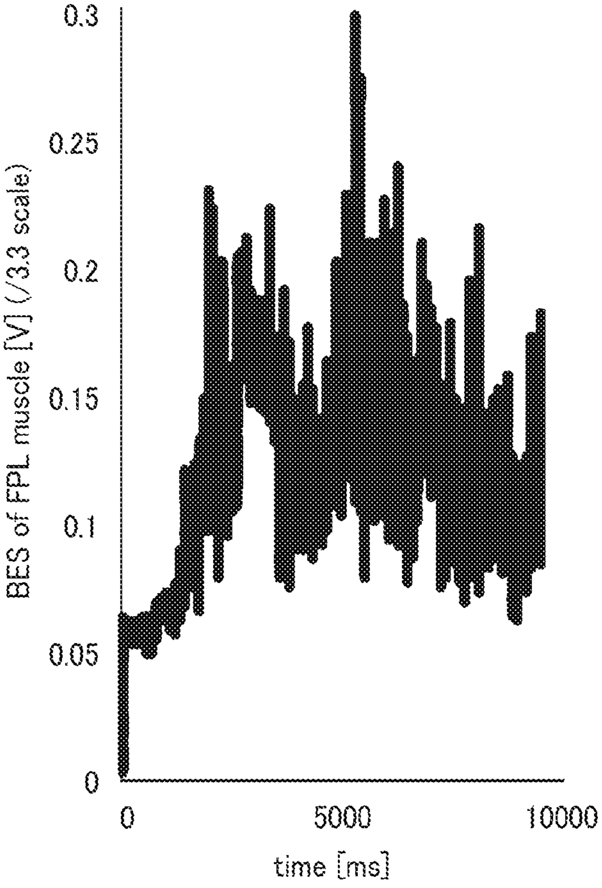

It was confirmed as the result of the above-described experiment that it was possible in all the trials to assist the bending and stretching movements to make the thumb come closer to the palm as illustrated in FIG. 12(B). FIG. 13(A) shows a representative example of the BES at that time. An average BES for five seconds, that is, five seconds to 10 seconds after the start of the motion support is calculated. An average value of the average BES of the five trials is 0.0640±0.0442 M under resting conditions (1/3.3 scale). Then, an average value of the average BES of the five trials in the case with the motion support by the present apparatus (1/3.3 scale) is 0.05620.00145 [V]. FIG. 13(B) shows a representative example of the BES when the thumb is flexed without using the wearable hand-finger motion support apparatus.

(6-3) Thumb's Fingertip Force Measurement Experiment

An assist force in the thumb flexion direction was measured in order to check whether or not it is possible to exert the assist force equal to or more than 4.29 [N] which is the force for the wearer to retain the 0.5 [kg] object by using the wearable hand-finger motion support apparatus 1 according to this embodiment.

With the tendon drive system using wires like the present apparatus, when the perpendicularity from the finger joint axis to the wire increases, the moment generated at the fingertip and the assist force increase. When the thumb bends with this wearable hand-finger motion support apparatus 1, the wire passes through the minimum distance between the fingertip retaining unit 10 and the auxiliary ring unit 11 and, therefore, the perpendicularity from the joint axis of the thumb to the wire becomes larger. This force weakens when the thumb extends.

Figure 14:
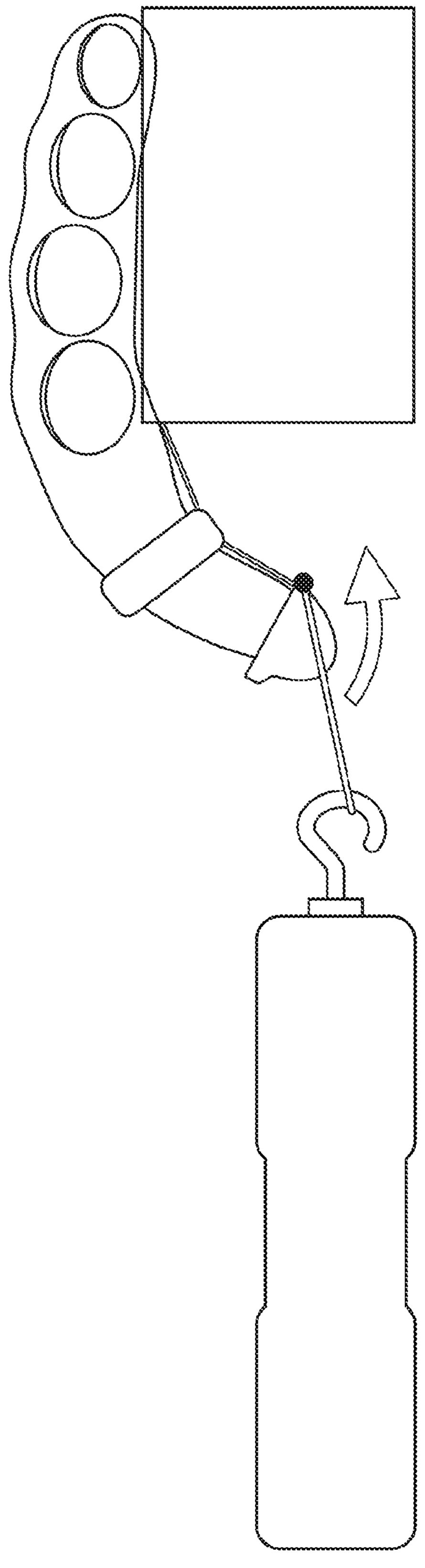
FIG. 14 is a conceptual diagram illustrating a fingertip force measurement experiment of the thumb.

Accordingly, as illustrated in FIG. 14, the wearer's left hand wearing the wearable hand-finger motion support apparatus 1 was placed on a block material so that the palm was kept in contact with the block material. Then, a force gauge which was fixed on a desk (for example, a digital force gauge ZP-500N which is a product manufactured by K.K. IMADA) was used and was wire-connected to the fingertip retaining unit of the extended thumb. The assist force was generated in the thumb flexion direction under this condition and the force at that time was measured five times.

According to the result of the above-described measurement, it was confirmed that an average of the fingertip force was 6.34±0.413 [N] and the force equal to or more than 4.29 [N] was measured in all the trials.

(6-4) Gripping Motion Experiment

In order to check whether the gripping motion is possible with only the thumb's movements, a cerebral apoplexy patient was assumed as the wearer and the wearable hand-finger motion support apparatus 1 was mounted on their left arm in a state of the wearer gripping their hand; and then the lateral gripping was performed. Under this circumstance, the wearable hand-finger motion support apparatus 1 was made to assist the extension and flexion of the wearer's thumb. Also, narrow and small objects such as narrow cylindrical objects like a key and a pen, and tubular objects were selected as targets to be gripped.

Figure 15:
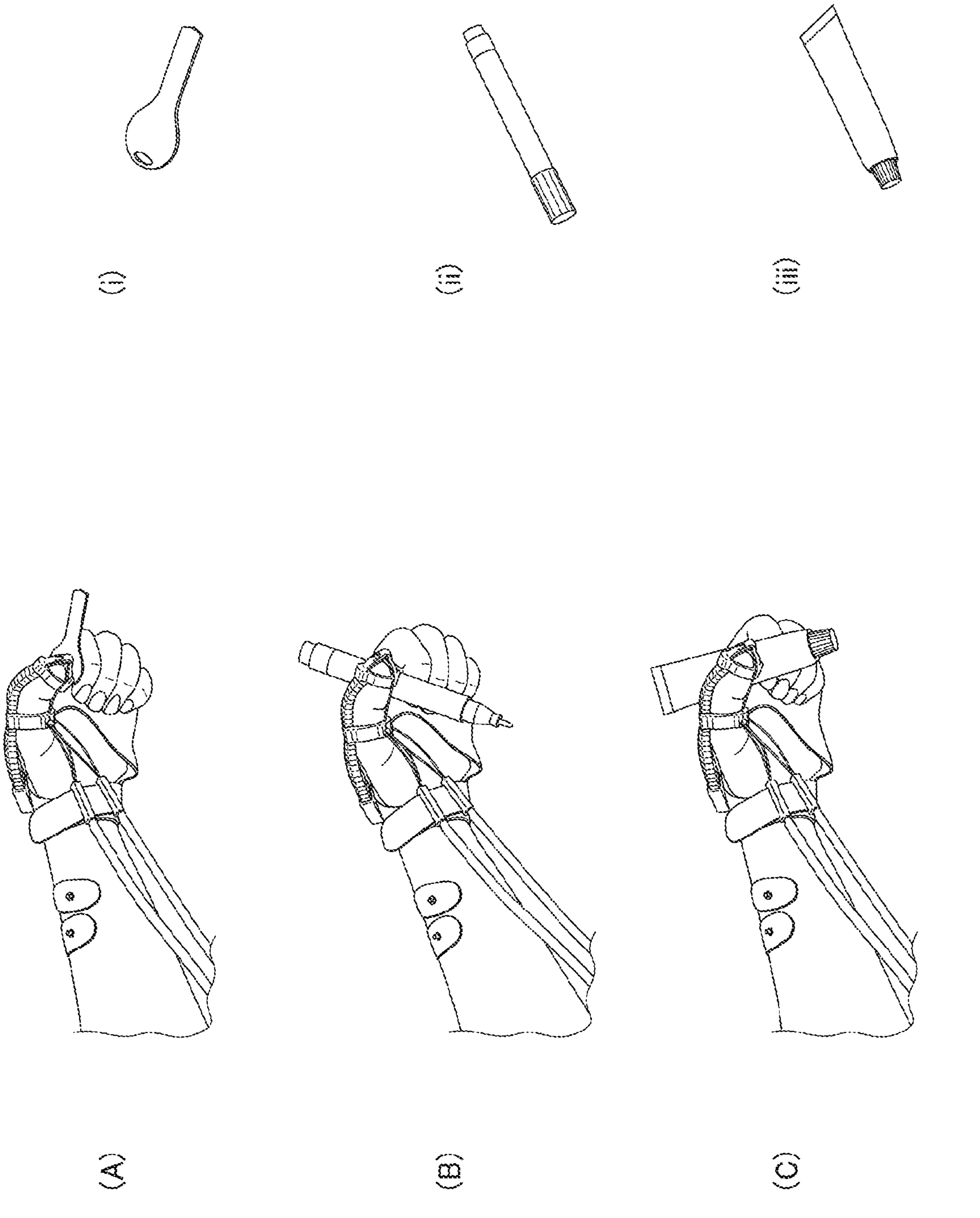

FIG. 15(A) to FIG. 15(C) show the results of the experiment. FIG. 15(A) shows a case of gripping a relatively narrow and small key; FIG. 15(B) shows a case of gripping a relatively narrow and long pen; and FIG. 15(C) shows a case of gripping a relatively narrow tubular object. Accordingly, it was confirmed that it is possible to grip a relatively thin object simply by using the wearable hand-finger motion support apparatus 1 to assist the movements of the wearer's thumb.

Figure 16:
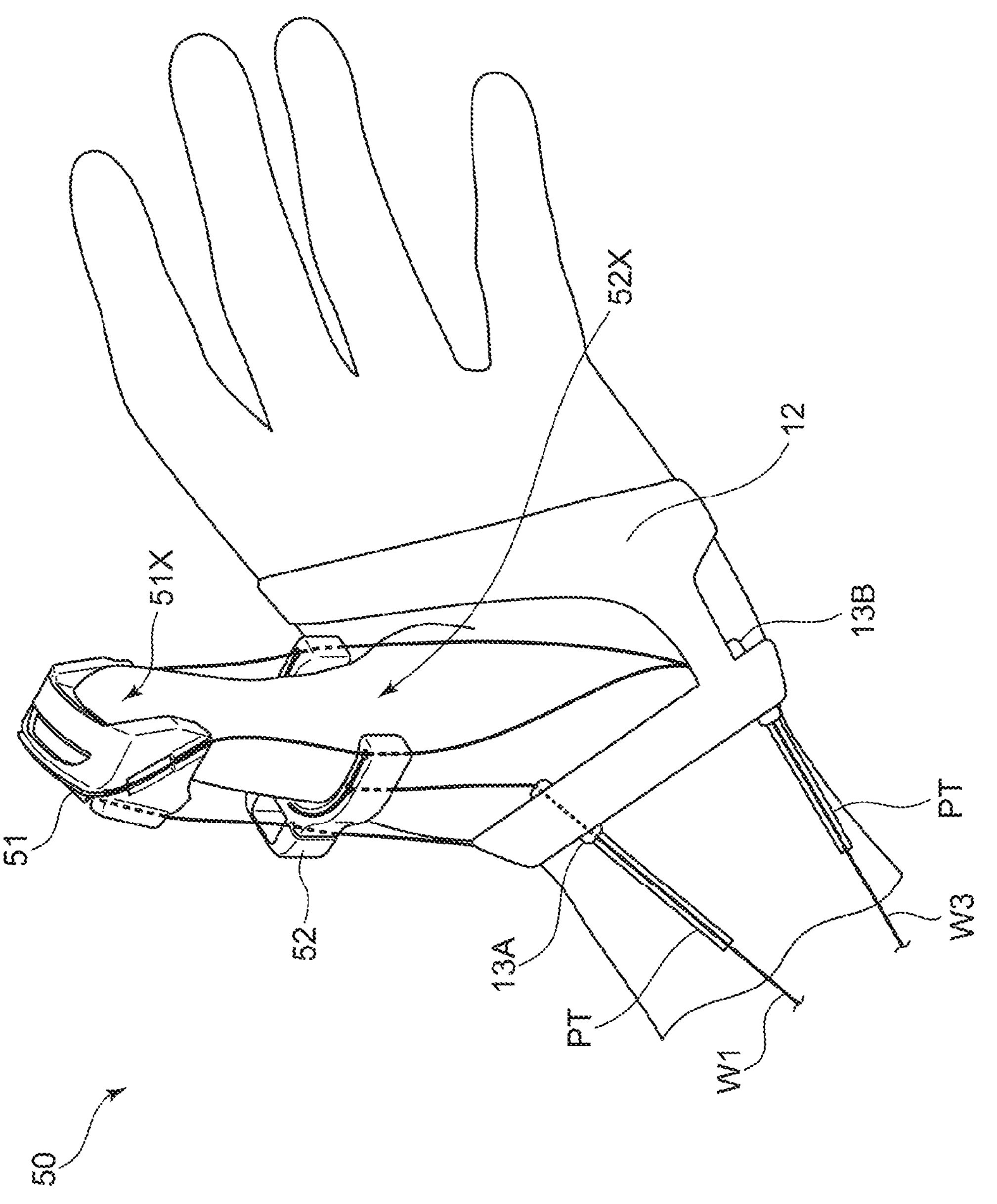
FIG. 16 is a schematic diagram illustrating the configuration of a wearable hand-finger motion support apparatus according to another embodiment of the present invention.

(7) Simultaneous Functions of Gripping Motion Assistance and Sensory Function Assistance (7-1) Thumb Motion Assistance Referring to FIG. 16 in which the same reference numerals as those in FIG. 4 and FIG. 5 are assigned to portions corresponding to those in FIG. 4 and FIG. 5, a wearable hand-finger motion support apparatus 50 has almost the same configuration as that of the aforementioned wearable hand-finger motion support apparatus 1, except that the structure of the fingertip retaining unit (the first retaining member) 10 and the auxiliary ring unit (the second retaining member) 11 is different and a control circuit for executing simultaneous functions of the gripping motion assistance and the sensory function assistance (a pressing force estimation unit 60 and a sensory transmission unit 70 which will be described later) is provided.

A fingertip retaining unit (first retaining member) 51 has an opening 51X to expose the pulp of the wearer's thumb and an auxiliary ring unit (second retaining member) 52 has an opening 52X to expose the palm side of the proximal phalanx of the thumb.

Figure 17:
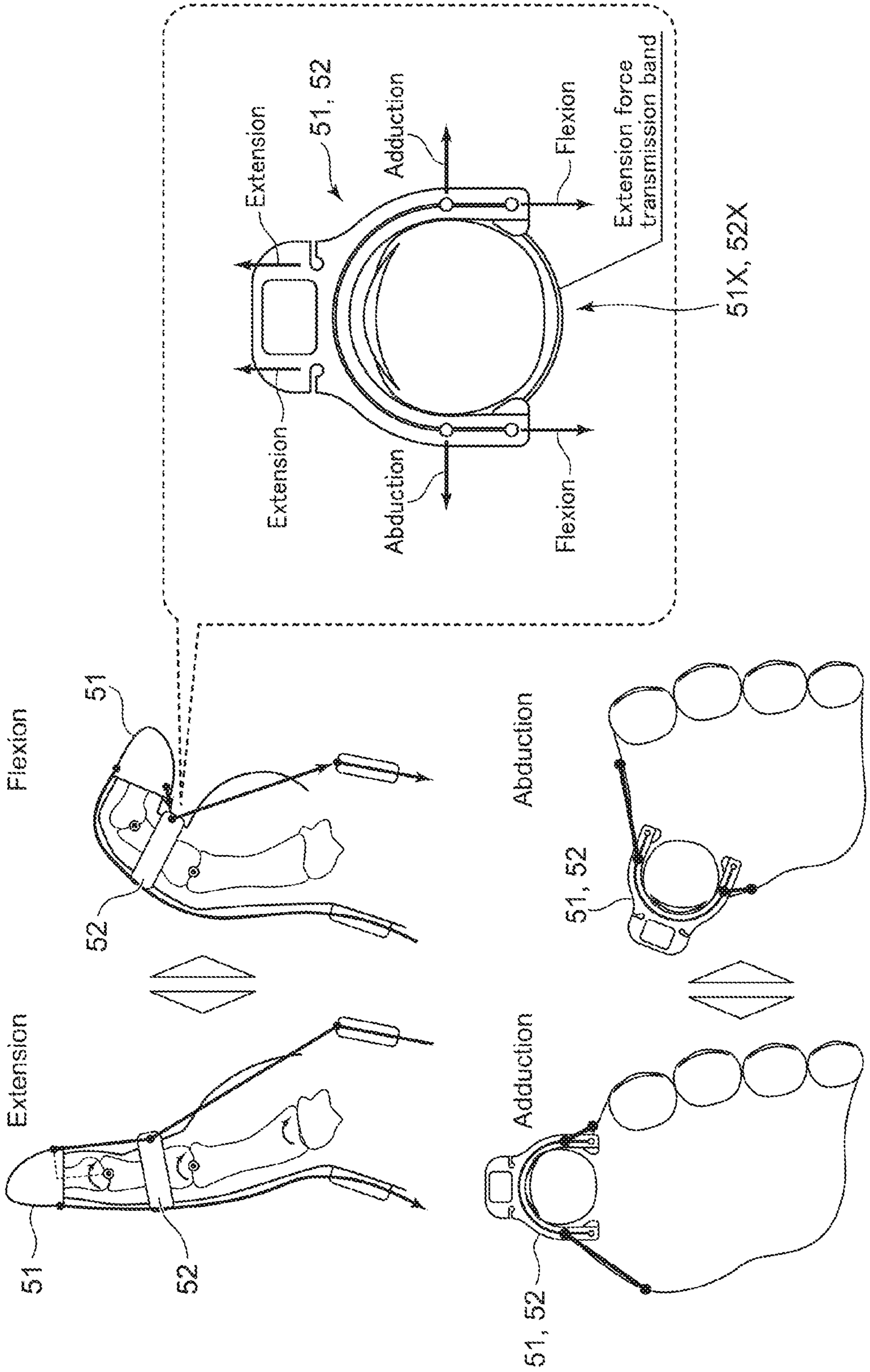
FIG. 17 is a schematic diagram illustrating a movement status when the wearable hand-finger motion support apparatus illustrated in FIG. 16 is mounted.

With this wearable hand-finger motion support apparatus, the openings 51X, 52X are formed in the fingertip retaining unit 51 and the auxiliary ring unit 52, respectively, so that as illustrated in FIG. 17, it is possible to directly contact the object, which is the target to be gripped, in the state where the pulp of the thumb is always exposed not only during the flexion movement or the extension movement of the wearer's thumb, but also the opposition movement or the adduction movement of the thumb.

Figure 18:
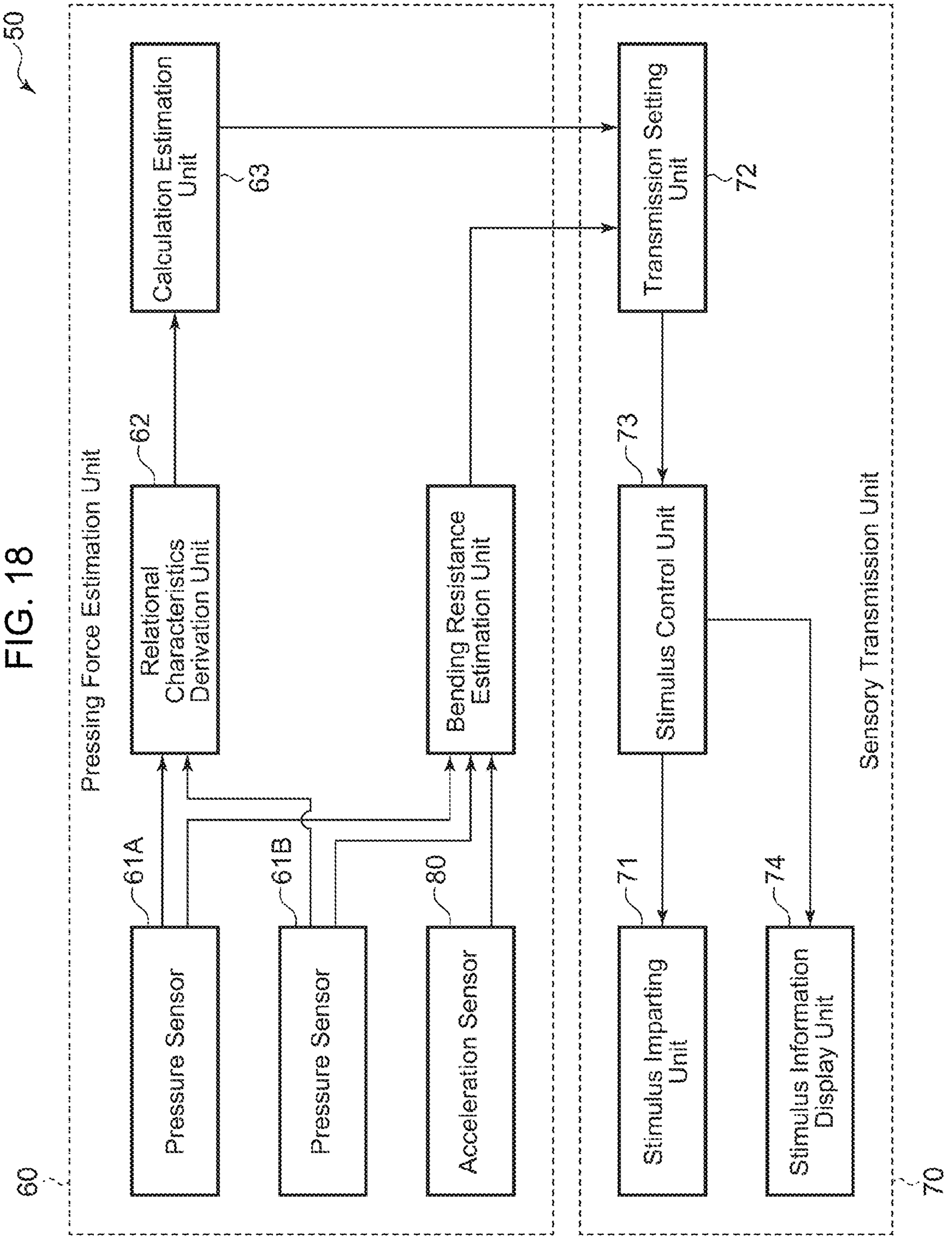
FIG. 18 is a block diagram illustrating a part of a control system for the wearable hand-finger motion support apparatus illustrated in FIG. 16.

Referring to FIG. 18, the wearable hand-finger motion support apparatus 50 is provided with the pressing force estimation unit 60 to be included in the fingertip retaining unit 51 and the external drive unit 22. When the wearer grips the object, the pressing force estimation unit 60 is designed to estimate a pressing force applied to the pulp of the thumb on the basis of a deformed state of the pulp of the thumb when contacting the object through the opening 51X in the fingertip retaining unit 51.

The pressing force estimation unit 60 has: a pair of pressure sensors 61A, 61B provided in the fingertip retaining unit 51; and a relational characteristics derivation unit 62 and a calculation estimation unit 63 which are provided in the external drive unit 22.

Figure 19:
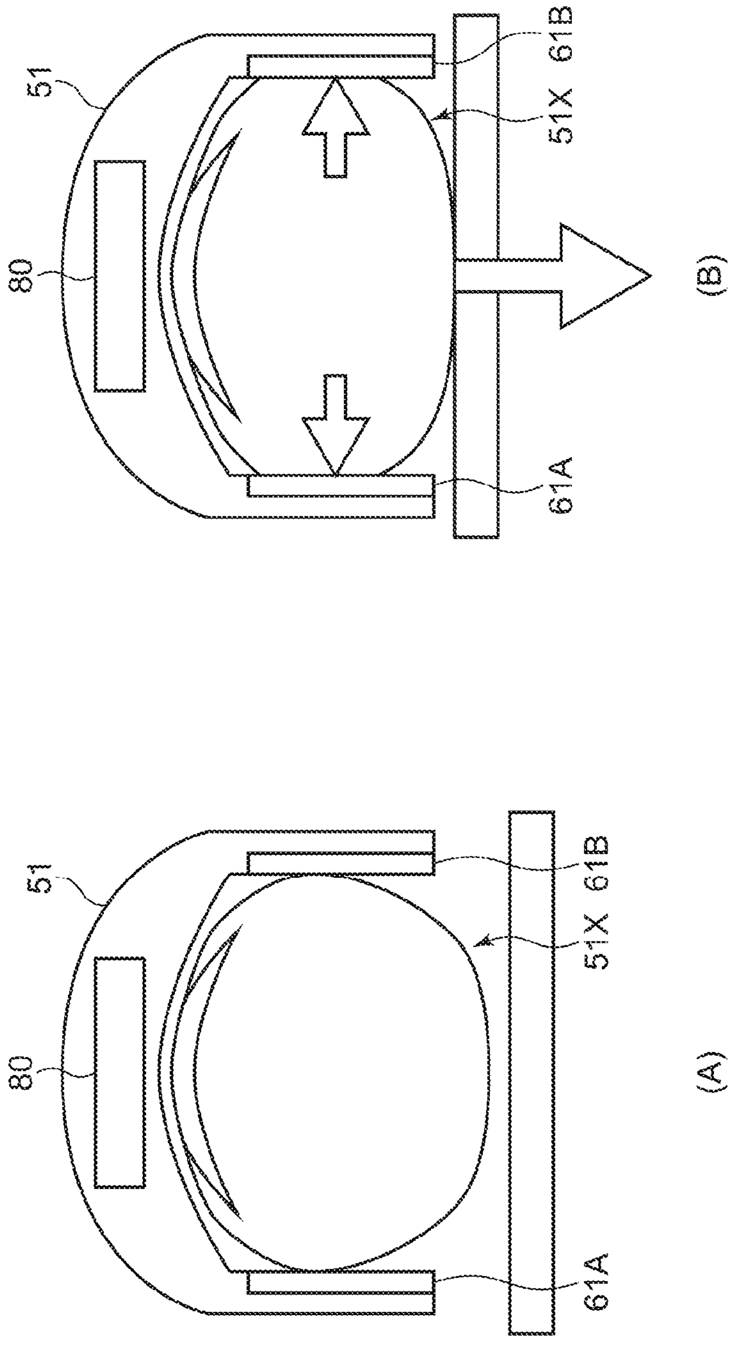
FIGS. 19(A) and 19(B) are schematic diagrams illustrating a sensor arrangement status in a fingertip retaining unit for the wearable hand-finger motion support apparatus illustrated in FIG. 16.

The pair of pressure sensors 61A, 61B are provided in the fingertip retaining unit 51 so that when they are mounted, they enter into contact with both side faces of the thumb as illustrated in FIG. 19(A); and each of the pair of pressure sensors 61A, 61B detects the pressing force applied from both the side faces of the thumb. For example, the pressure sensor 61A, 61B is composed of a strain gauge and converts a mechanical strain amount according to an external force into an electric quantity. Incidentally, as described later, not only the pair of pressure sensors 61A, 61B, but also an acceleration sensor 80 is embedded in the fingertip retaining unit 51 on the back side of the thumb.

Specifically, referring to FIG. 19(B), at the time point where the fingertip of the thumb wearing the fingertip retaining unit 51 enters into contact with the object, a reaction force against the pressing force onto the object is applied to the pulp of the thumb and then is applied on sensor faces of the pair of pressure sensors 61A, 61B as a deformation force in directions of both sides of the fingertip of the thumb.

The relational characteristics derivation unit 62: measures respective actual measurement values of a plurality of levels of the load applied to the pulp of the thumb; and derives relational characteristics between the load applied to the pulp of the thumb and the detection result of the pair of pressure sensors 61A, 61B on the basis of the detection result of the pair of pressure sensors 61A, 61B obtained for each of the actual measurement values.

Practically, a test for measuring characteristics of the force on the side faces as caused by a horizontal deformation of the finger when contacting the object was conducted in order to derive the relational characteristics by the relational characteristics derivation unit 62. This testing method is a method of placing the finger wearing the pressure sensors (the strain gauges) 61A, 61B and leaving them statically on a jig, applying the load of 1 to 6 [N] from above to the pulp of the fingertip by using an application device (which is not shown in the drawing), and measuring output values of the pressure sensors 61A, 61B three times for each of them.

Figure 20:
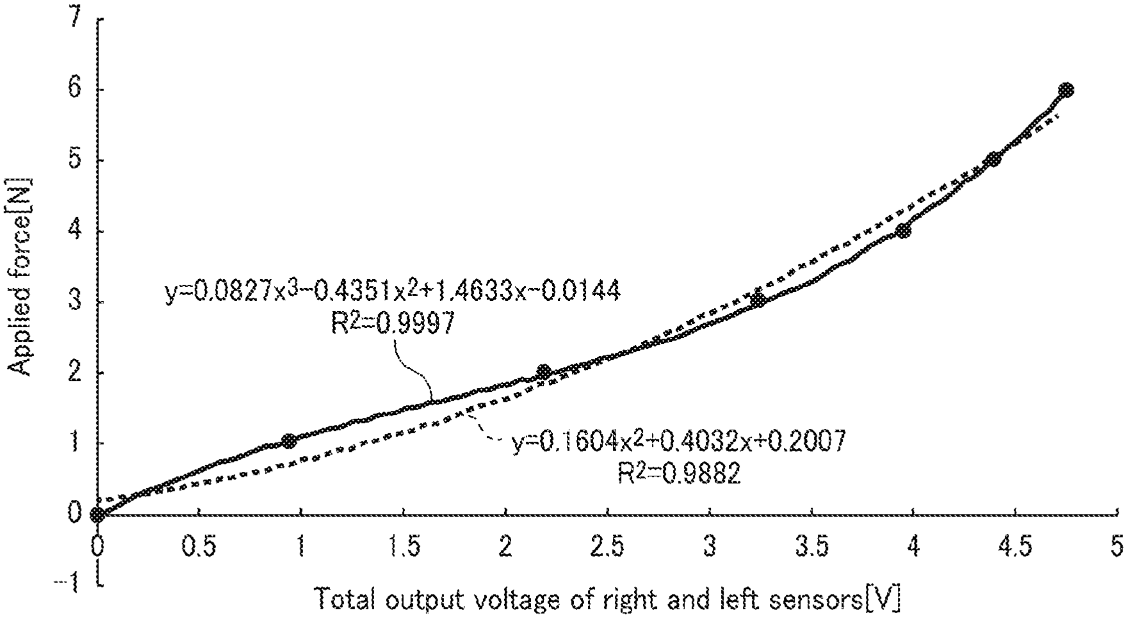
FIG. 20 is a graph indicating the relation between a load applied to a finger pulp and an output from pressure sensors.

A graph indicated in FIG. 20 shows the relation between the load applied to the finger pulp and the output of the pressure sensors 61A, 61B. When x represents the output of the pressure sensors 61A, 61B and y represents the load applied to the finger pulp, it was indicated that the relation can be estimated by a relational expression composed of polynomials such as Expression (2) and Expression (3) below.

[Math. 2]

$$y=0.1604x^2+0.4032x+0.2007 \quad (2)$$

[Math. 3]

$$y=0.0827x^3-0.4351x^2+1.4633x-0.0144 \quad (3)$$

Figure 21:
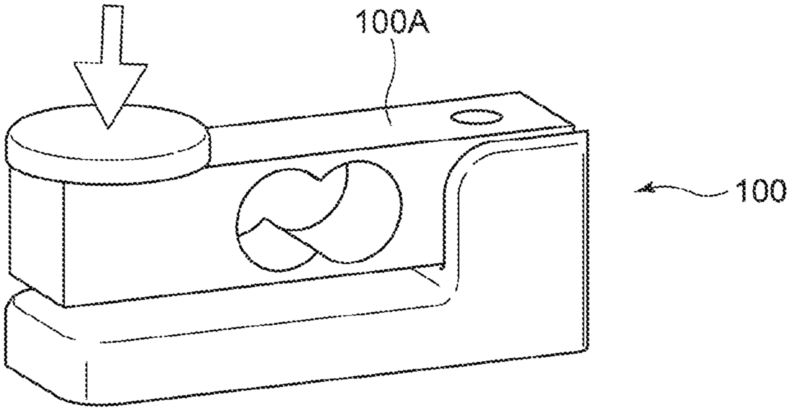
FIG. 21 is a schematic diagram illustrating an external configuration of a calibration apparatus by using a load cell.

Incidentally, regarding the pressure sensors 61A, 618, a calibration apparatus 100 which uses a micro load cell 100A as illustrated in FIG. 21 is used to calibrate a sensor output value for each individual wearer.

Subsequently, a measurement performance evaluation test of the pressure sensors 61A, 61B was conducted. Specifically, a test for checking basic performance was conducted to check that the pressure sensors 61A, 61B are capable of measuring the force without obstructing the pulp of the finger.

Specifically speaking, the aforementioned calibration apparatus 100 (FIG. 21) was used in a state where the pair of pressure sensors 61A, 61B were mounted on both sides of a test subject's forefinger; and a motion to press the forefinger against the load cell 100A and a motion to release the forefinger were repeated alternately for 30 seconds after the calibration. The measurement was conducted five times and an average of a root mean square error (RMSE: Root Mean Square Error) between the estimated value and the measured value of the load cell 100A was calculated.

Relational expressions for output values $f_R$, $f_L$ of the right and left pressure sensors 61A, 61B and a fingertip force $F_{fingertip}$ are expressed by polynomials such as Expressions (3) and (4) below and the measurement was conducted five times for each of them.

[Math. 4]

$$F_{fingertip}=a(fR+fL)^2+b(fR+fL)+c \quad (4)$$

[Math. 5]

$$F_{fingertip}=a(fR+fL)^3+b(fR+fL)^2+c(fR+fL)+d \quad (5)$$

In the above-mentioned Expressions (3) and (4), each of a, b, c, and d is a coefficient obtained by connecting plots of the actual measurement value; and, for example, Expression (3) which is a quadratic polynomial can be obtained as a specific relational expression like Expression (1), and Expression (4) which is a cubic polynomial can be obtained as a specific relational expression like Expression (2).

Under this circumstance, since it is known that softness of the human's fingers changes at the time of low load such as 1 to 2 [N] and at the time of heavier load, it is believed that the cubic polynomial which has an inflection point within the range of 1 to 2 [N] can express the characteristics of the finger much better and will make the error smaller.

Figure 22:
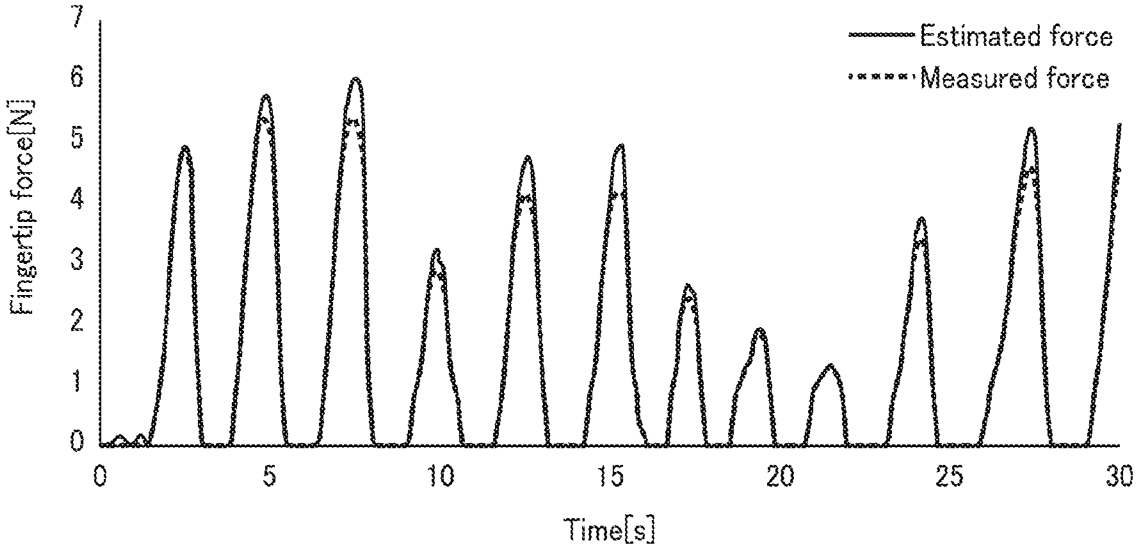
FIG. 22 is a graph indicating the estimation of a fingertip force when using a cubic polynomial.

FIG. 22 indicates a graph which estimates the fingertip force when the cubic polynomial like Expression (4) is actually used. Regarding the graph in FIG. 22, a horizontal axis represents time [s] and a vertical axis represents the fingertip force [N]; and as a waveform F2 which is the estimated value indicates almost similar waveform to a waveform F1 which is the measured value of the load cell 100A, you can see that the fingertip force can be estimated. Since the pressure sensors 61A, 61B has monotonicity for the fingertip force of 0 to 5 [N], it is sufficient for practical use as sensory feedback information.

Figure 23:
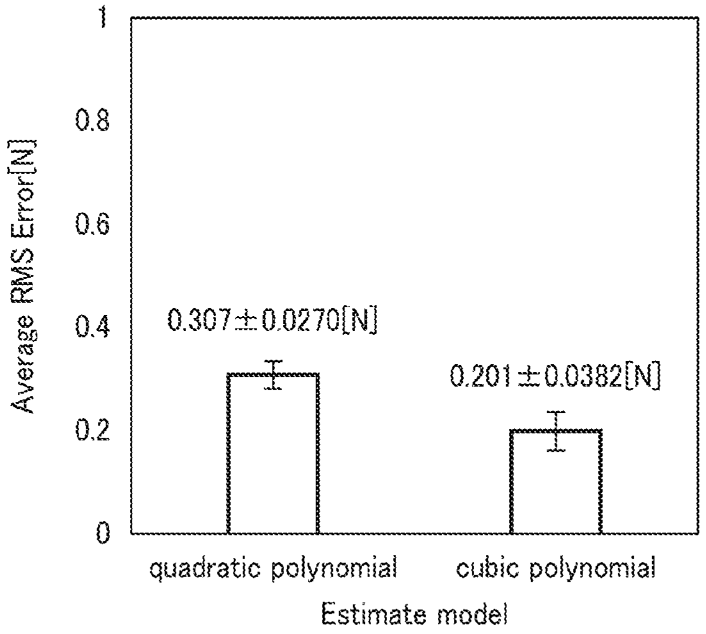
FIG. 23 is a graph indicating an average RMSE between estimated values and measured values of the load cell, and its standard error.

Incidentally, referring to FIG. 23, regarding Expression (4) which is the cubic polynomial, an average of the root mean square error (RMSE) between the estimated value and the measured value of the load cell 100A, and its standard error was 0.201±0.0382 (NJ. On the other hand, regarding Expression (3) which is the quadratic polynomial, an average of the root mean square error (RMSE) between the estimated value and the measured value of the load cell 100A, and its standard error was 0.307±0.0270 [N].

Then, the calculation estimation unit 63 (FIG. 18) calculates and estimates the pressing force onto the pulp of the thumb when contacting the object, on the basis of the relational characteristics (the aforementioned cubic polynomial) calculated by the relational characteristics derivation unit 62.

As a result, the wearable hand-finger motion support apparatus 50 can measure the pressing force onto the object while causing the pulp of the wearer's thumb to directly contact the object, which is the target to be gripped, without obstructing the pulp of the wearer's thumb.

Accordingly, the wearer makes the pulp of the thumb directly contact the object and presses the pulp against the object, so that it becomes possible to acquire haptic information regarding the object without impeding the mechanical properties of the skin which prevent deformation or slippage caused in accordance with the shape of the object. Particularly, when the wearer has the hand-finger paralysis, it becomes possible to realize the gripping motion assistance based on the haptic information of the thumb and it is thereby very useful.

Consequently, the wearable hand-finger motion support apparatus 50 can estimate the gripping force using the thumb by measuring the force on the side faces of the finger as caused by the horizontal deformation of the wearer's thumb.

(7-2) Thumb's Sensory Transmission Feedback

This wearable hand-finger motion support apparatus 50 is further provided with a sensory transmission unit 70 (FIG. 18), so that it is designed to feed back and transmit the pressing force, which is estimated by the calculation estimation unit 63 for the pressing force estimation unit 60, as a sensation to the pulp of the wearer's thumb.

This sensory transmission unit 70 has a stimulus imparting unit 71 with terminal groups for imparting physical (such as mechanical, electrical, and thermal) stimuli to a specified body surface of the wearer (for example, an arm surface or a shoulder surface on the non-paralyzed arm side).

Furthermore, the sensory transmission unit 70 has a transmission setting unit 72 and a stimulus control unit 73. The transmission setting unit 72 sets a sensory size and a transmission pattern to be transmitted to the wearer according to the pressing force applied to the pulp of the thumb which is obtained from the calculation estimation unit 63 for the pressing force estimation unit 60. The stimulus control unit 73 controls each terminal group of the stimulus imparting unit 71 in accordance with the setting content by the transmission setting unit 72.

As a result, with the wearable hand-finger motion support apparatus 50, the wearer can recognize the stimulus according to the pressing force onto the pulp of the thumb as a sensation via the specified body surface.

Incidentally, the stimulus control unit 73 may be provided with a stimulus information display unit 74 which displays information according to the status of the physical stimuli by the stimulus imparting unit 71. This stimulus information display unit 74 may be configured of, for example, LED elements whose luminance changes according to the setting content by the transmission setting unit 72. Consequently, it becomes possible to visually recognize the sensory size and the transmission pattern, which are transmitted to the wearer by the stimulus imparting unit 71, externally via the stimulus information display unit 74.

(7-3) Estimation of Bending Resistance of Object

Furthermore, the wearable hand-finger motion support apparatus 50 is designed so that when the object which is the target to be gripped is something not hard, but soft, bending resistance of the object is also fed back and transmitted to the wearer at the same time as the pressing force onto the pulp of the thumb by estimating the bending resistance of the object.

The pressing force estimation unit 60 for this wearable hand-finger motion support apparatus 50 is further provided with an acceleration sensor 80 and a bending resistance estimation unit 81 (FIG. 18). The acceleration sensor 80: is provided in the fingertip retaining unit 51 so that it is to be located at the back of the thumb when being mounted as illustrated in FIG. 19(A) described earlier; and detects acceleration of the thumb in the gripping direction.

Moreover, the bending resistance estimation unit 81 estimates the bending resistance of the object in contact with the pulp of the thumb on the basis of the detection result by the pair of pressure sensors 61A, 61B and the detection result by the acceleration sensor 80.

The sensory transmission unit 70 feeds back and transmits the pressing force, which is estimated by the calculation estimation unit 63 for the pressing force estimation unit 60, as the sensation to the pulp of the wearer's thumb in a state combined with the bending resistance of the object which is estimated by the bending resistance estimation unit 81.

Consequently, the wearable hand-finger motion support apparatus 50 can estimate the bending resistance of the object in contact with the pulp of the thumb depending on how much the acceleration of the thumb in the gripping direction by the acceleration sensor 80 reacts from the timing to start the detection by the pair of pressure sensors 61A, 61B.

(7-4) Gripping Motion Assistance with Other Fingers Added to and Including Thumb Furthermore, the wearable hand-finger motion support apparatus 50 may be also applied similarly to at least one or more fingers (a forefinger, a middle finger, a ring finger, and a little finger) other than the wearer's thumb.

Figure 24:
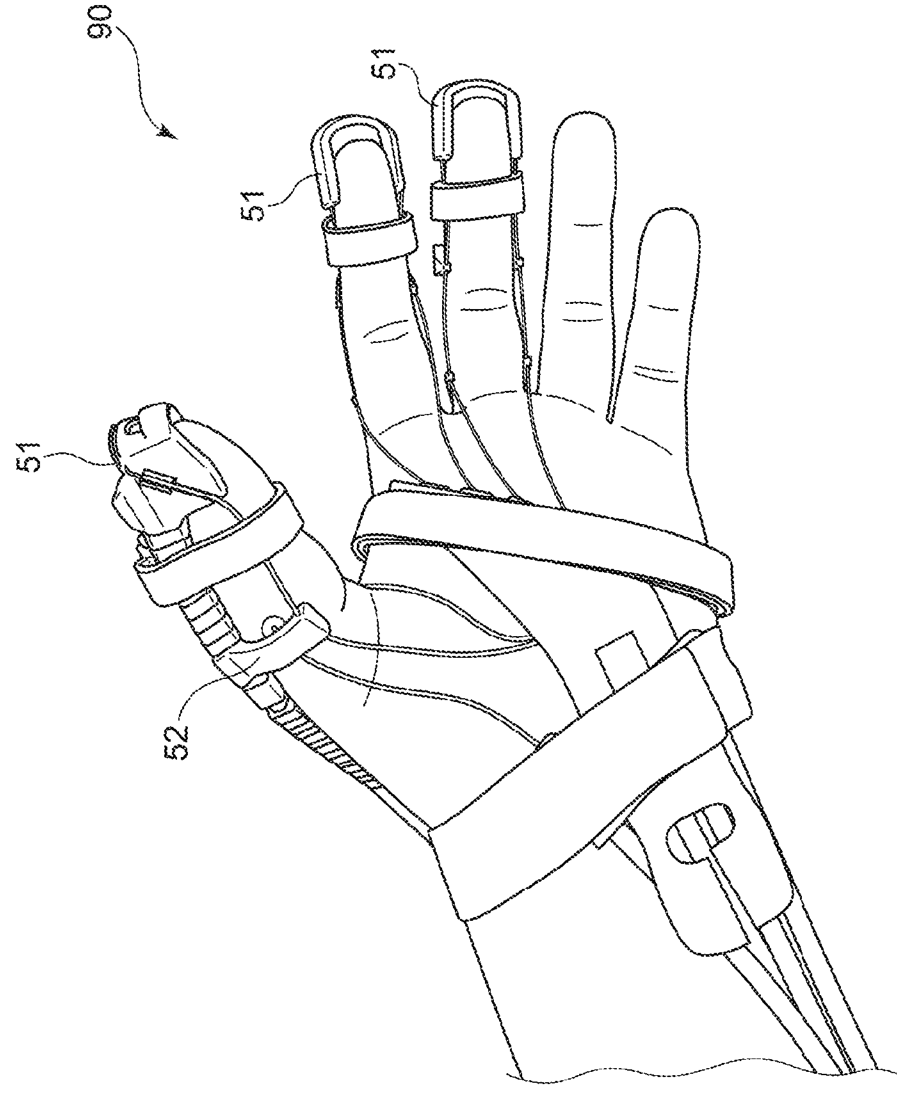
FIG. 24 is a schematic diagram illustrating the configuration of a wearable hand-finger motion support apparatus designed to be mounted on multiple fingers.
Figure 25:
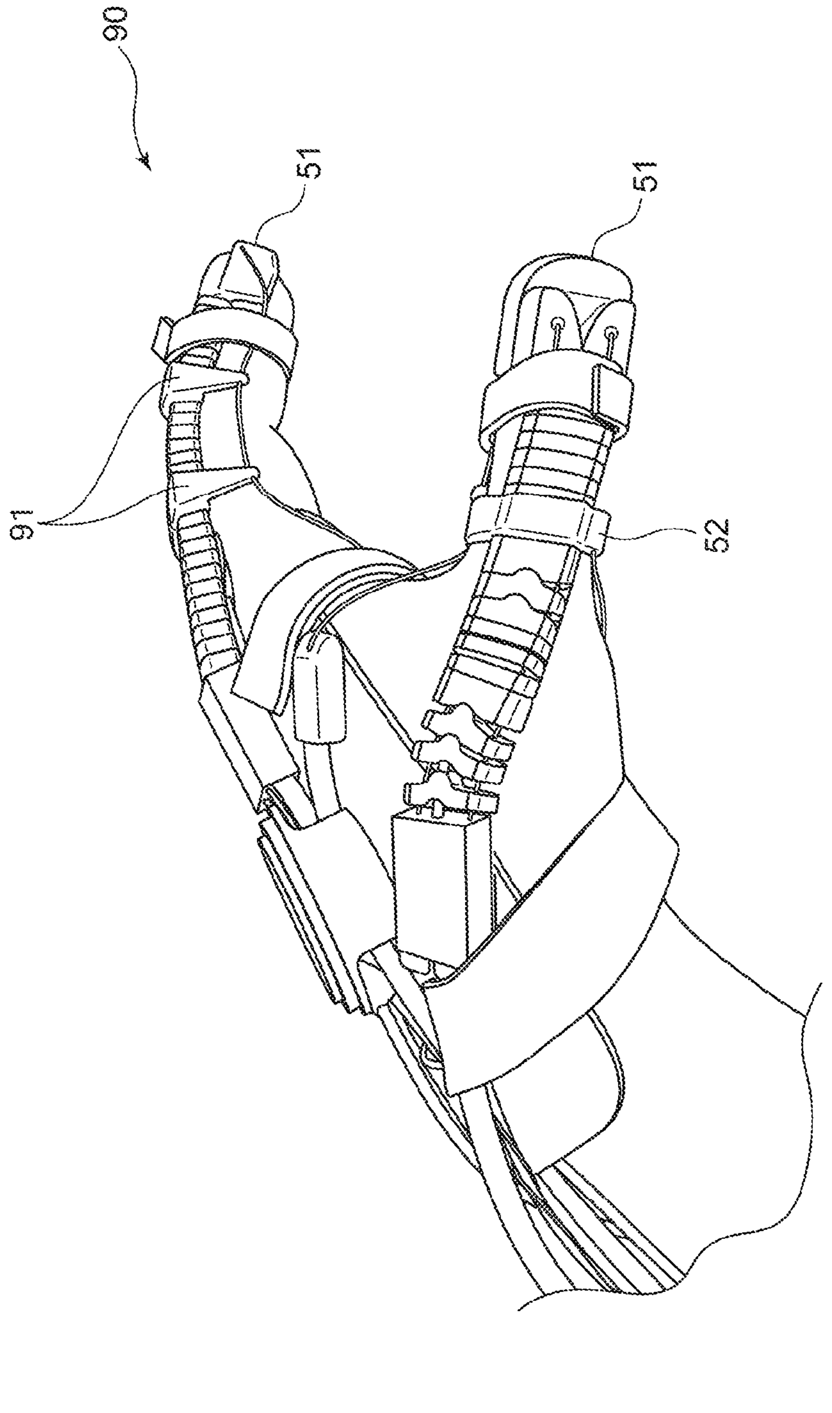
FIG. 25 is a schematic diagram illustrating the configuration of the wearable hand-finger motion support apparatus designed to be mounted on multiple fingers.

Regarding a wearable hand-finger motion support apparatus 90 illustrated in FIG. 24 and FIG. 25, the fingertip retaining unit (the first retaining member) 51 is mounted at a fingertip of each of the forefinger and the middle finger in addition to the wearer's thumb, and the flexion wire W3 and the extension wire W4 are pulled out from the fingertip retaining unit, are routed through wire guides 91, and are pulled along the dorsal side of the finger.

The drive control unit 24 controls the linear member drive unit 20 to alternately pull or relax the flexion wire W3 or the extension wire W4 corresponding to the relevant movement in order to cause the intrinsic muscles and/or the extrinsic muscles of each relevant finger, which are required for the flexion movement or the extension movement of the index finger and the middle finger on which the fingertip retaining unit 51 is mounted, to generate an assist force.

As a result, the wearable hand-finger motion support apparatus 90 can construct, also for at least one or more fingers other than the wearer's thumb, the system for acquiring the haptic information and assisting the gripping motion without disturbing the skin properties of the pulp or the sensory input.

Under this circumstance, a test to check the performance to control the object gripping force was conducted by using the wearable hand-finger motion support apparatus 90 regarding which the thumb, the forefinger, and the middle finger are targets to mount the fingertip retaining unit 51.

Firstly, after mounting the wearable hand-finger motion support apparatus 90 on the left hand of the wearer in a relaxed state, sensor output values of the pressure sensors 61A, 61B are calibrated by the calibration apparatus 100 (FIG. 21) which uses the micro load cell 100A as described earlier with respect to not only the thumb, but also the forefinger and the middle finger.

Figure 26:
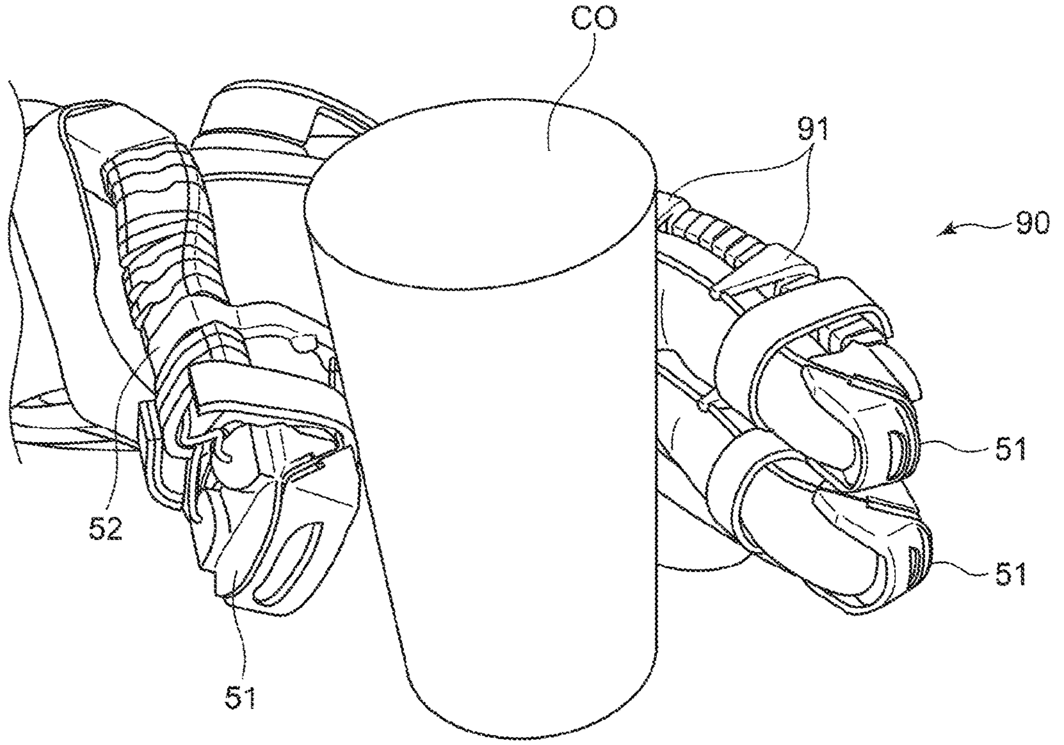
FIGS. 26(A) and 26(B) are schematic diagrams illustrating a state where the motion to grip a cylindrical object is supported, and a graph indicating the relation between time and a gripping force.
Figure 26:
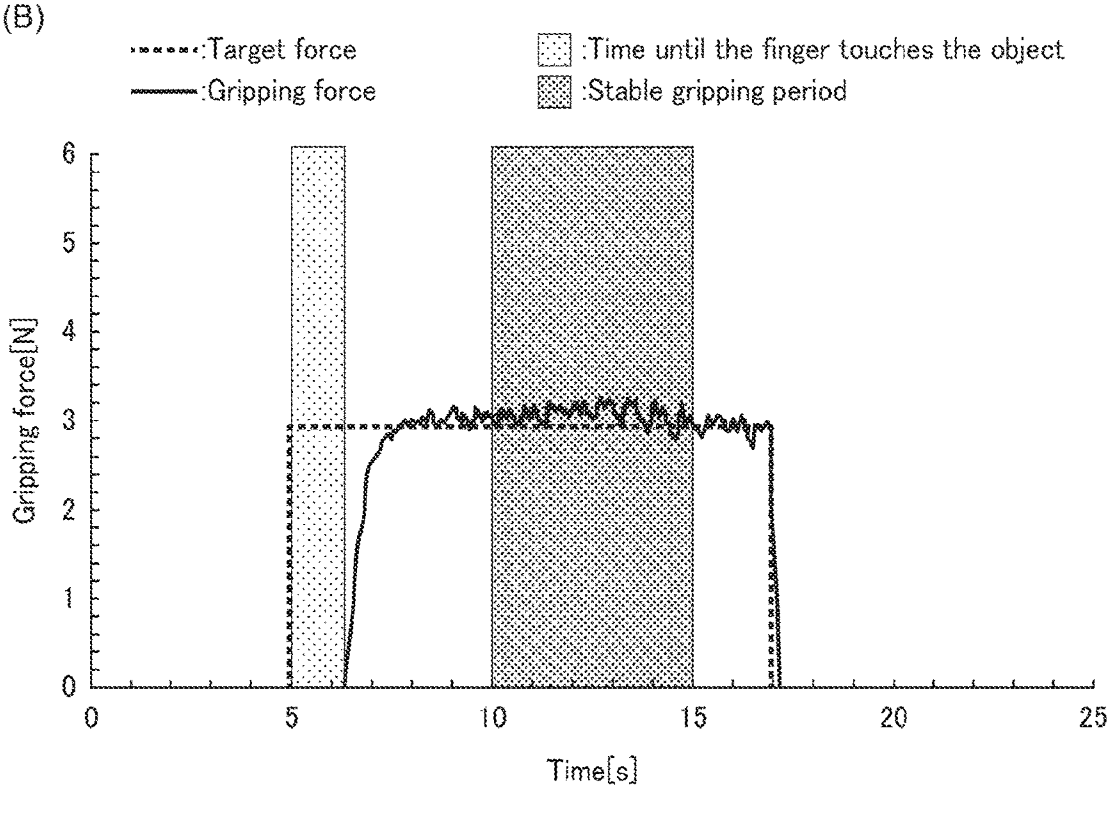

Then, the gripping motion relative to a cylindrical object CO is assisted as illustrated in FIG. 26(A) and errors relative to the target gripping force regarding the gripping force for 10 to 15 [s] are calculated. FIG. 26(B) shows a graph indicating the relation between time and the gripping force in the case where the target gripping force is 3 [N]. Regarding this graph, the force from 5 [s] after the wearer started gripping the object, until 10 to 15 [s] when the gripping state became stable was measured. In this graph, a dotted line represents the target gripping force, while a solid line represents the measured gripping force.

Figure 27:
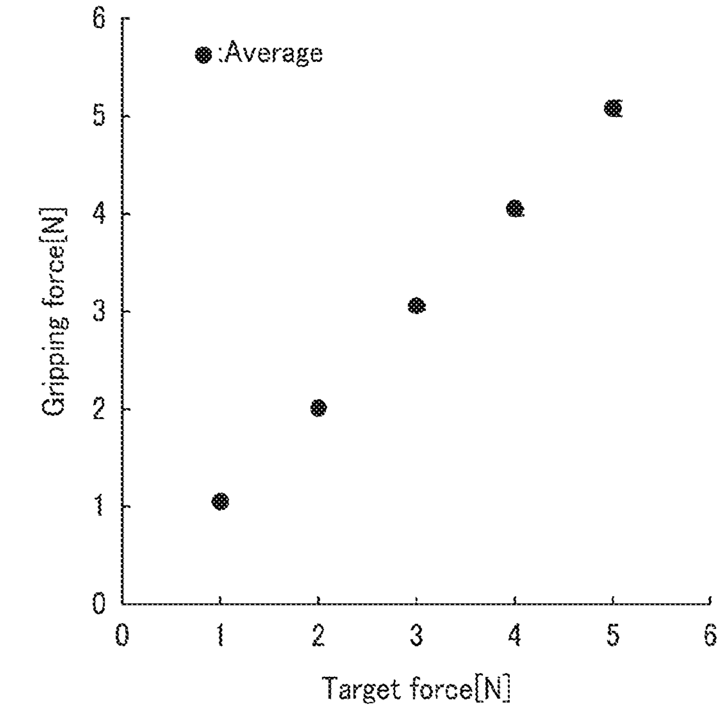
FIGS. 27(A) and 27(B) show graphs indicating the relation between a measured gripping force and a target gripping force, and a graph indicating errors relative to the target gripping force.
Figure 27:
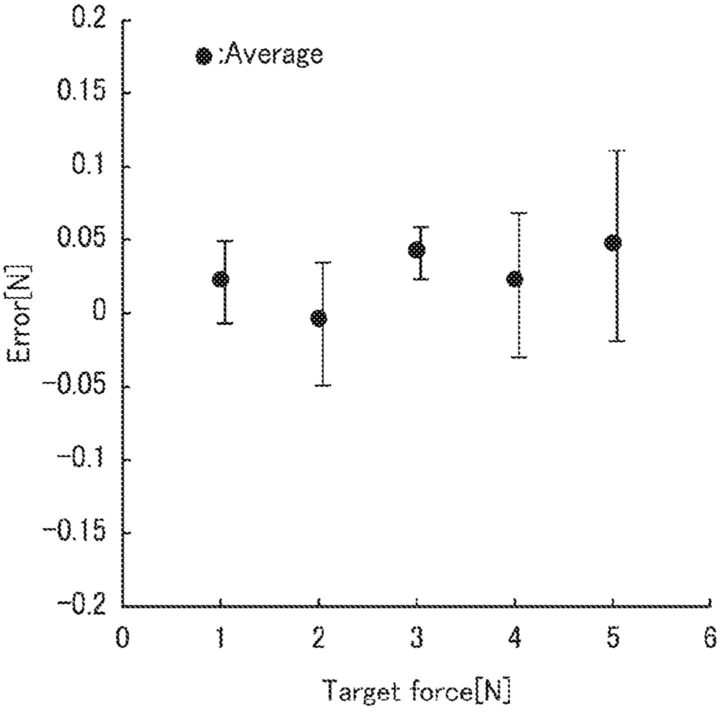

FIG. 27(A) shows the relation between the measured gripping force and the target gripping force and FIG. 27(B) shows the errors relative to the target gripping force. It was confirmed that an average of the errors was within the range of ±0.11 [N] including a standard deviation. It was also confirmed that the maximum value of the errors relative to the target value is 4.81% when the target gripping force is 1.0 [N].

Consequently, the force which is approximately 1.33 times as large as the required minimum force as the human's gripping force can be exerted even in consideration of 5% errors relative to the target value, so that it was confirmed that it is sufficiently possible to exert the gripping force which will not cause the object to be dropped.

Furthermore, when objects which become targets to be gripped have different shapes, a test was conducted to check if the relevant object can be gripped with the target gripping force which is set for each object, and if it is possible to grip the object according to the shape of the object which is the target to be gripped.

A testing method is to: assist the hand-finger motions in a state where the wearable hand-finger motion support apparatus 90 is mounted on a left hand in a relaxed state; and grip the object, keep it in air, and release it. Gripping is performed by switching between the adduction and the abduction of the thumb according to the shape of the object which is the target to be gripped. It is considered that the object can be gripped when the gripped object is kept in air for 5 [s].

Figure 28:
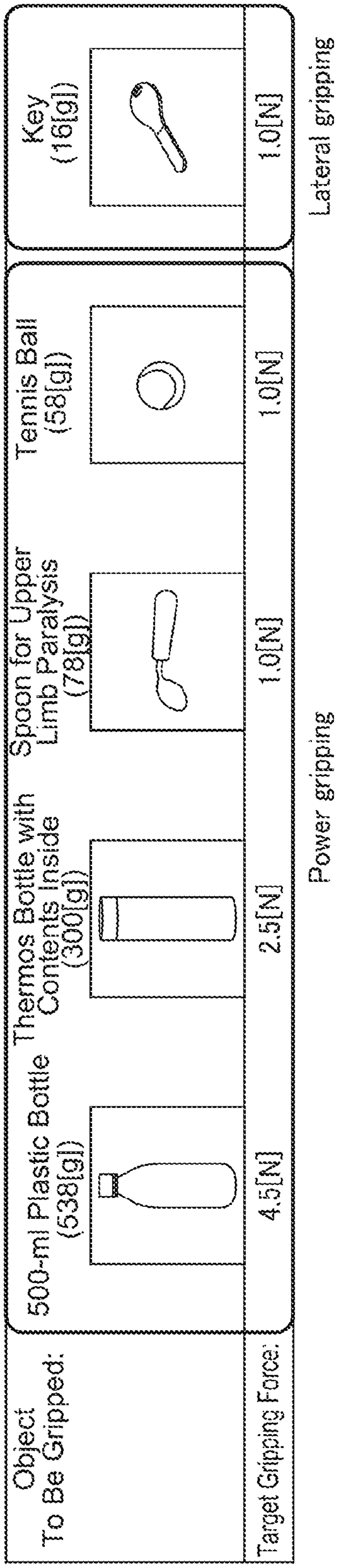
FIG. 28 is a schematic diagram indicating types of targets to be gripped.
Figure 29:
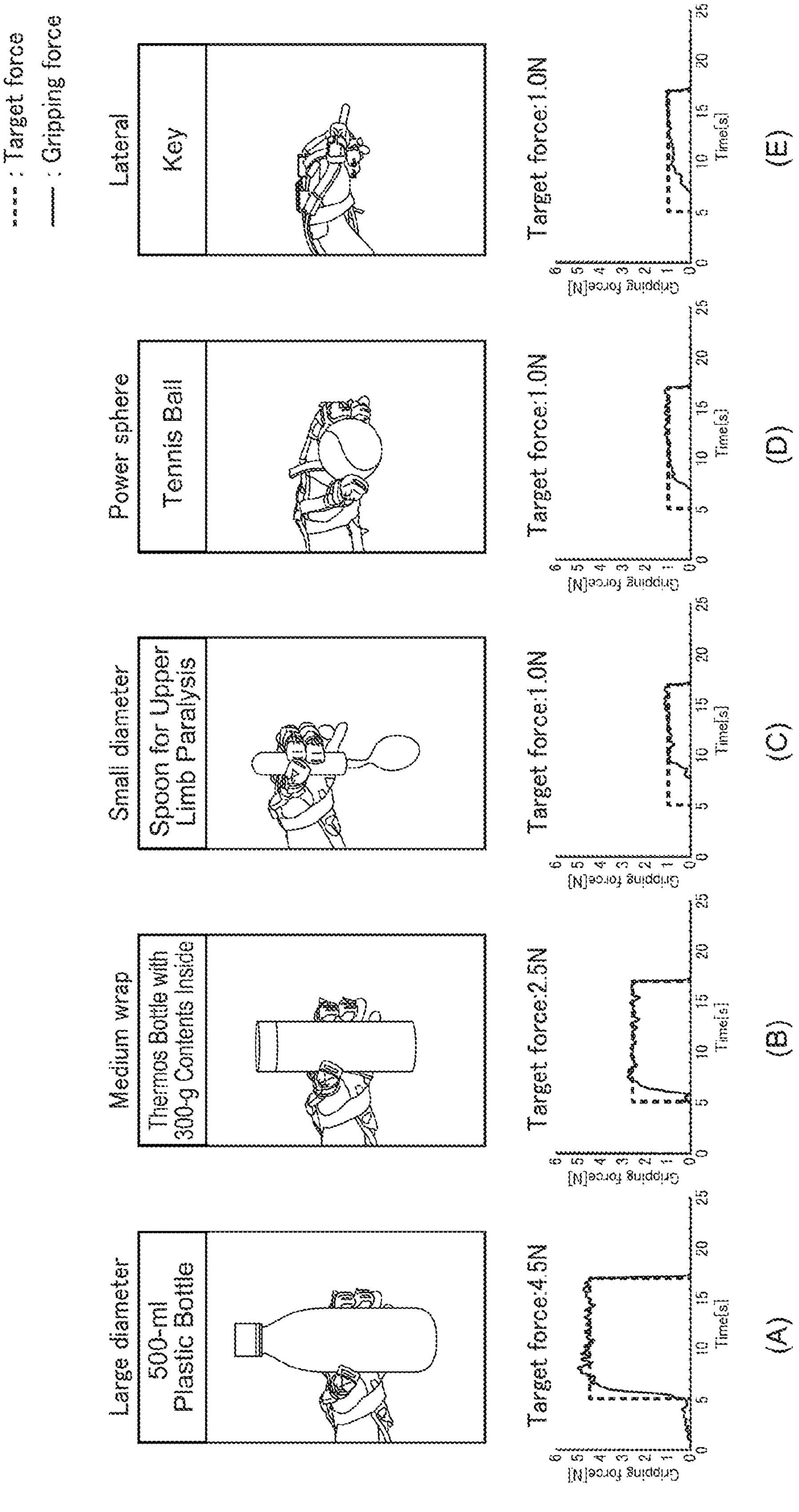
FIGS. 29(A) to 29(E) show schematic diagrams and graphs of the gripping state indicating test results of FIG. 28.

Referring to FIG. 28, the test was conducted by selecting five kinds of objects, that is, a 500-ml plastic bottle (weight: 538 [g]), a thermos bottle with contents inside (weight: 300 [g]), a spoon for upper limb paralysis (weight: 78 [g]), a tennis ball (weight: 58 [g]), and a key (weight: 16 [g]) as the targets to be gripped and setting 4.5 [N], 2.5 [N], 1.0 [N], 1.0 [N], and 1.0 [N] respectively as their target gripping force.

The test results are indicated as graphs for comparing the measured gripping force with the target gripping force respectively in FIG. 29(A) to FIG. 29(E). It was proven from the respective graphs that either one of the cylindrical object or spherical object with different diameters (gripping by moving the thumb to the opposite side), and the thin-type object (gripping by adducting the thumb) as the target to be gripped can be gripped with the target gripping force.

Consequently, it was confirmed that the wearable hand-finger motion support apparatus 90 makes it possible to assist the adduction and abduction movements of the thumb in addition to the flexion and extension movements of the hand and fingers and grip objects of various shapes.

(8) Other Embodiments

Incidentally, this embodiment has described the case where the wearable hand-finger motion support apparatus 1 with the configuration including the following elements is applied: the fingertip retaining unit 10 which is mounted to cover the tip of the wearer's thumb; the auxiliary ring unit 11 which is mounted to be wound around the proximal phalanx of the thumb; and the guiding connection unit 13 for the Velcro (registered trademark) glove 12 which is mounted to retain the root of the thumb and the wrist leading to the root in close contact with each other; however, the present invention is not limited to this example and apparatuses with various other configurations may be applied as long as they can assist the thumb's movements without impeding the degree of freedom of the thumb when gripping the target object in everyday life.

Moreover, this embodiment has described the case where regarding the linear member drive unit 20, each of the extended portions of the opposition movement wire W1 and the adduction wire W2, which are pulled out from the auxiliary ring unit 11 as the base point, is fixed and connected to the first pulley P1; however, the present invention is not limited to this example and the opposition movement wire W1 and the adduction wire W2 may be configured of the same one continuous wire.

Similarly, the case has been described where regarding the linear member drive unit 20, each of the extended portions of the flexion wire W3 and the extension wire W4, which are pulled out from the fingertip retaining unit 10 as the base point via the auxiliary ring unit 11, is fixed and connected to the second pulley P2; however, the present invention is not limited to this example and the flexion wire W3 and the extension wire W4 may be configured of the same one continuous wire.

REFERENCE SIGNS LIST

1, 50, 90: wearable hand-finger motion support apparatus
10, 51: fingertip retaining unit
11, 52: auxiliary ring unit
12: Velcro (registered trademark) glove
13: guiding connection unit
20: linear member drive unit
20A: first actuator
20B: second actuator
21: signal detection unit
22: external drive unit
23: movement judgment unit
24: drive control unit
30 first slide retaining unit
31: second slide retaining unit
40: polyarticular structure
60: pressing force estimation unit
61A, 61B: pressure sensors
62 relational characteristics derivation unit
63: calculation estimation unit
70: sensory transmission unit
71: stimulus imparting unit
72: transmission setting unit
73: stimulus control unit
74: stimulus information display unit
80: acceleration sensor
91: wire guide
W1: opposition movement wire
W2: adduction wire
W3: flexion wire
W4: extension wire
PT: protective tube
P1: first pulley
P2: second pulley

The invention claimed is:

1. A wearable hand-finger motion support apparatus comprising:

a first retaining member mounted to cover a tip of a wearer's thumb;

a second retaining member mounted to be wound around a proximal phalanx of the thumb;

a third retaining member mounted to retain a root of the thumb and a wrist leading to the root in close contact with each other;

a plurality of linear members, one end of which is fixed to either the first retaining member or the second retaining member, and each of which is routed through the third retaining member along a surface of the thumb and is extended;

a linear member drive unit that drives an extended portion of each linear member to pull or relax the extended portion of each linear member;

a signal detection unit that is located on a body surface corresponding to intrinsic muscles and/or extrinsic muscles of the wearer's thumb and detects an EMG signal or a biosignal to cause the thumb to perform motions;

a movement judgment unit that judges either one of an opposition movement, an adduction movement, a flexion movement, or an extension movement of the thumb by the wearer on a basis of a detection result by the signal detection unit; and a drive control unit that controls the linear member drive unit to pull or relax each linear member corresponding to the movement judged by the movement judgment unit in order to cause the intrinsic muscles and/or the extrinsic muscles of the thumb, which are required for the movement judged by the movement judgment unit, to generate an assist force, wherein the plurality of linear members are fixed to the second retaining member and have an opposition movement wire and an adduction wire which are respectively pulled out from the proximal phalanx of the thumb and are routed through the third retaining member toward a direction along an opponens pollicis muscle and an adductor pollicis muscle existing in a palm including the thumb;

wherein the signal detection unit detects the EMG signal or the biosignal from the body surface corresponding to the opponens pollicis muscle and the adductor pollicis muscle among the intrinsic muscles of the thumb;

wherein the movement judgment unit judges the opposition movement or the adduction movement of the thumb by the wearer on the basis of the detection result by the signal detection unit;

wherein the drive control unit controls the linear member drive unit to alternately pull or relax the opposition movement wire or the adduction wire in synchronization with timing to start the opposition movement or the adduction movement of the thumb as judged by the movement judgment unit;

wherein the linear member drive unit is provided on a separate body from the first retaining member to the third retaining member, includes a first pulley with a specified diameter to which respective extended portions of the opposition movement wire and the adduction wire that are pulled out from the second retaining member as a base point are fixed and connected, and a first actuator with its output axis which engages with the first pulley, and causes a rotating force of the output axis of the first actuator to be transmitted to the opposition movement wire or the adduction wire via the first pulley;

wherein the linear member drive unit has a first slide retaining unit which retains the first pulley and the first actuator so that the first pulley and the first actuator can freely slide integrally with each other;

wherein the first slide retaining unit is connected to the third retaining member via a fixed-length tube into which the opposition movement wire and the adduction wire are inserted respectively; and wherein lengths of the opposition movement wire and the adduction wire between the first retaining member and the second retaining member can be adjusted by causing the first pulley and the first actuator to slide relative to the first slide retaining unit.

2. A wearable hand-finger motion support apparatus comprising:

a first retaining member mounted to cover a tip of a wearer's thumb;

a second retaining member mounted to be wound around a proximal phalanx of the thumb;

a third retaining member mounted to retain a root of the thumb and a wrist leading to the root in close contact with each other;

a plurality of linear members, one end of which is fixed to either the first retaining member or the second retaining member, and each of which is routed through the third retaining member along a surface of the thumb and is extended;

a linear member drive unit that drives an extended portion of each linear member to pull or relax the extended portion of each linear member;

a signal detection unit that is located on a body surface corresponding to intrinsic muscles and/or extrinsic muscles of the wearer's thumb and detects an EMG signal or a biosignal to cause the thumb to perform motions;

a movement judgment unit that judges either one of an opposition movement, an adduction movement, a flexion movement, or an extension movement of the thumb by the wearer on a basis of a detection result by the signal detection unit; and a drive control unit that controls the linear member drive unit to pull or relax each linear member corresponding to the movement judged by the movement judgment unit in order to cause the intrinsic muscles and/or the extrinsic muscles of the thumb, which are required for the movement judged by the movement judgment unit, to generate an assist force, wherein the plurality of linear members are fixed to the first retaining member and have a flexion wire and an extension wire, which are pulled out from the tip of the thumb and are respectively routed through the third retaining member via the second retaining member in directions along a pulp side and a dorsal side;

wherein the signal detection unit detects an EMG signal or a biosignal from a body surface corresponding to a flexor pollicis longus muscle and an extensor pollicis longus muscle existing in an upper arm via tendons from the thumb, from among the extrinsic muscles of the thumb;

wherein the movement judgment unit judges the flexion movement or the extension movement of the thumb by the wearer on the basis of the detection result by the signal detection unit;

wherein the drive control unit controls the linear member drive unit to alternately pull or relax the flexion wire or the extension wire in synchronization with timing to start the flexion movement or the extension movement of the thumb as judged by the movement judgment unit;

wherein the linear member drive unit is provided on a separate body from the first retaining member to the third retaining member, includes a second pulley with a specified diameter to which respective extended portions of the flexion wire and the extension wire that are pulled out from the first retaining member as a base point via the second retaining member are fixed and connected, and a second actuator with its output axis which engages with the second pulley, and causes a rotating force of the output axis of the second actuator to be transmitted to the flexion wire or the extension wire via the second pulley;

wherein the linear member drive unit has a second slide retaining unit which retains the second pulley and the second actuator so that the second pulley and the second actuator can freely slide integrally with each other;

wherein the second slide retaining unit is connected to the third retaining member via a fixed-length tube into which the flexion wire and the extension wire are inserted respectively; and wherein lengths of the flexion wire and the extension wire between the first retaining member and the second retaining member can be adjusted by causing the second pulley and the second actuator to slide relative to the second slide retaining unit.

3. The wearable hand-finger motion support apparatus according to claim 2, further comprising a polyarticular structure in which links aligned in series are coupled together so as to be rotatable relatively to each other and all the links are integrated together so as to be deformable in a freely bendable manner, wherein the polyarticular structure is provided from the first retaining member, to which one end of the extension wire is fixed, is routed through the second retaining member, and extends to the third retaining member in a state where the extension wire is inserted into each of all the links.

4. The wearable hand-finger motion support apparatus according to claim 3, wherein the polyarticular structure is designed so that the links are coupled together so as to be freely separable from each other, and a length of the polyarticular structure can be adjusted by inserting or pulling out a desired number of the links.

5. The wearable hand-finger motion support apparatus according to claim 2, wherein the wearable hand-finger motion support apparatus is also applied to one or more fingers of the wearer other than the thumb, including a forefinger, a middle finger, a ring finger, and a little finger in a same manner; and wherein the drive control unit controls the linear member drive unit to alternately pull or relax the flexion wire or the extension wire corresponding to a flexion movement or an extension movement of each finger, other than the thumb, on which the first retaining member is mounted in order to cause intrinsic muscles and/or extrinsic muscles of each finger which are required for the flexion movement or the extension movement of the finger to generate an assist force.

6. A wearable hand-finger motion support apparatus comprising:

a first retaining member mounted to cover a tip of a wearer's thumb;

a second retaining member mounted to be wound around a proximal phalanx of the thumb;

a third retaining member mounted to retain a root of the thumb and a wrist leading to the root in close contact with each other;

a plurality of linear members, one end of which is fixed to either the first retaining member or the second retaining member, and each of which is routed through the third retaining member along a surface of the thumb and is extended;

a linear member drive unit that drives an extended portion of each linear member to pull or relax the extended portion of each linear member;

a signal detection unit that is located on a body surface corresponding to intrinsic muscles and/or extrinsic muscles of the wearer's thumb and detects an EMG signal or a biosignal to cause the thumb to perform motions;

a movement judgment unit that judges either one of an opposition movement, an adduction movement, a flexion movement, or an extension movement of the thumb by the wearer on a basis of a detection result by the signal detection unit; and a drive control unit that controls the linear member drive unit to pull or relax each linear member corresponding to the movement judged by the movement judgment unit in order to cause the intrinsic muscles and/or the extrinsic muscles of the thumb, which are required for the movement judged by the movement judgment unit, to generate an assist force, wherein the first retaining member has an opening formed therein in order to expose a pulp of the wearer's thumb;

wherein the wearable hand-finger motion support apparatus comprises:

a pressing force estimation unit that estimates a pressing force applied to the pulp of the thumb on the basis of a deformed state of the pulp of the thumb when contacting an object through the opening; and a sensory transmission unit that feeds back and transmits the pressing force, which is estimated by the pressing force estimation unit, as a sensation felt by the pulp of the wearer's thumb, wherein the pressing force estimation unit includes:

a pair of pressure sensors that are provided at the first retaining member to enter into contact with both side faces of the thumb when being mounted, and respectively detect a pressing force applied from both side faces of the thumb;

a relational characteristics derivation unit that measures each of actual measurement values of a plurality levels of load applied to the pulp of the thumb and derives relational characteristics between the load applied to the pulp of the thumb and a detection result of the pair of pressure sensors on the basis of the detection result of the pair of pressure sensors, which is obtained for each actual measurement value; and a calculation estimation unit that calculates and estimates the pressing force applied to the pulp of the thumb when contacting the object on the basis of the relational characteristics calculated by the relational characteristics derivation unit.

7. The wearable hand-finger motion support apparatus according to claim 6, wherein the sensory transmission unit includes:

a stimulus imparting unit that has terminal groups for imparting physical stimuli to a specified body surface of the wearer;

a transmission setting unit that sets a sensory size and a transmission pattern to be transmitted to the wearer according to the pressing force which is applied to the pulp of the thumb and is obtained from the calculation estimation unit; and a stimulus control unit that controls each terminal of each one of the terminal group for the stimulus imparting unit in accordance with setting content by the transmission setting unit.

8. The wearable hand-finger motion support apparatus according to claim 7, wherein the pressing force estimation unit further includes:

an acceleration sensor that is provided at the first retaining member so as to be located at a back of the thumb when being mounted and detects acceleration of the thumb in a gripping direction; and a bending resistance estimation unit that estimates bending resistance of the object before entering into contact with the pulp of the thumb on the basis of the detection result by the pair of pressure sensors and a detection result by the acceleration sensor, wherein the transmission setting unit for the sensory transmission unit sets the pressing force estimated by the calculation estimation unit as the sensory size and the transmission pattern to be transmitted to the wearer in a state combined with the bending resistance of the object which is estimated by the bending resistance estimation unit.

* * * * *